(12) United States Patent
Ichikawa et al.

(10) Patent No.: US 8,367,298 B2
(45) Date of Patent: Feb. 5, 2013

(54) SALT AND PHOTORESIST COMPOSITION CONTAINING THE SAME

(75) Inventors: Koji Ichikawa, Toyonaka (JP); Masako Sugihara, Nishinomiya (JP); Hiromu Sakamoto, Ibaraki (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 267 days.

(21) Appl. No.: 12/835,427

(22) Filed: Jul. 13, 2010

(65) Prior Publication Data

US 2011/0014568 A1 Jan. 20, 2011

(30) Foreign Application Priority Data

Jul. 16, 2009 (JP) ................. 2009-167674

(51) Int. Cl.
*G03F 7/00* (2006.01)
*G03F 7/004* (2006.01)
*G03F 7/028* (2006.01)
*G03F 7/40* (2006.01)

(52) U.S. Cl. ............. 430/270.1; 430/330; 430/311; 430/331; 430/913

(58) Field of Classification Search .......... 430/270.1, 430/913, 311, 330, 331
See application file for complete search history.

(56) References Cited

U.S. PATENT DOCUMENTS

| 7,611,822 | B2 * | 11/2009 | Takemoto | ........... 430/270.1 |
| 2003/0194639 | A1 | 10/2003 | Miya et al. | |
| 2006/0194982 | A1 | 8/2006 | Harada et al. | |
| 2010/0304292 | A1 * | 12/2010 | Ichikawa et al. | ........... 430/270.1 |
| 2010/0304293 | A1 * | 12/2010 | Ichikawa et al. | ........... 430/270.1 |
| 2010/0304294 | A1 * | 12/2010 | Ichikawa et al. | ........... 430/270.1 |
| 2010/0304296 | A1 * | 12/2010 | Ichikawa et al. | ........... 430/270.1 |

FOREIGN PATENT DOCUMENTS

| JP | 2010134279 A | * | 6/2010 |
| JP | 2010134445 A | * | 6/2010 |
| JP | 2010140014 A | * | 6/2010 |
| JP | 2010152341 A | * | 7/2010 |

OTHER PUBLICATIONS

Machine translation of JP 2010-140014 (no date).*
Machine translation of JP 2010-134279 (no date).*

* cited by examiner

*Primary Examiner* — Amanda C. Walke
(74) *Attorney, Agent, or Firm* — Birch, Stewart, Kolasch & Birch, LLP

(57) ABSTRACT

A salt having a divalent group represented by the formula (aa):

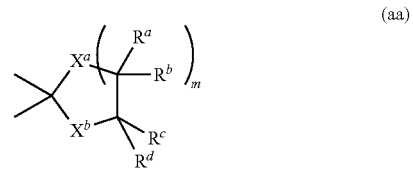

wherein $X^a$ and $X^b$ independently each represent —O— or —S—,
$R^a$, $R^b$, $R^c$ and $R^d$ independently each represent a hydrogen atom, a C1-C4 alkyl group or a C1-C4 alkoxy group, and m represents 1 or 2.

10 Claims, No Drawings

SALT AND PHOTORESIST COMPOSITION CONTAINING THE SAME

This nonprovisional application claims priority under 35 U.S.C. §119(a) on Patent Application No. 2009-167674 filed in JAPAN on Jul. 16, 2009, the entire contents of which are hereby incorporated by reference.

FIELD OF THE INVENTION

The present invention relates to a salt and a photoresist composition containing the same.

BACKGROUND OF THE INVENTION

A chemically amplified positive resist composition used for semiconductor microfabrication employing a lithography process contains an acid generator comprising a compound generating an acid by irradiation.

US 2003/0194639 A1 discloses triphenylsulfonium (1-adamantyl)methoxycarbonyldifluoromethanesulfonate and a photoresist composition comprising a resin and triphenylsulfonium (1-adamantyl)methoxycarbonyldifluoroethane as an acid generator.

SUMMARY OF THE INVENTION

An object of the present invention is to provide a novel salt and a photoresist composition containing the same.

The present invention relates to the followings:

<1> A salt having a divalent group represented by the formula (aa):

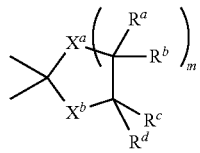

(aa)

wherein $X^a$ and $X^b$ independently each represent —O— or —S—,
$R^a$, $R^b$, $R^c$ and $R^d$ independently each represent a hydrogen atom, a C1-C4 alkyl group or a C1-C4 alkoxy group, and m represents 1 or 2;

<2> The salt according to <1>, wherein the salt has a divalent group represented by the formula (a1):

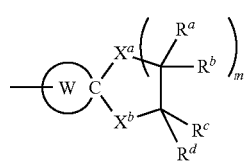

(a1)

wherein $X^a$, $X^b$, $R^a$, $R^b$, $R^c$, $R^d$ and m are the same as defined in <1>, and W represents a C3-C36 saturated ring in which one or more —$CH_2$— can be replaced by —O—, —S—, —CO— or —$SO_2$—, and in which one or more hydrogen atoms can be replaced by a hydroxyl group, a C1-C12 alkyl group, a C1-C12 alkoxy group, a C3-C12 alicyclic hydrocarbon group or a C6-C10 aromatic hydrocarbon group;

<3> The salt according to <1> or <2>, wherein the salt consists of an anion having the divalent group represented by the formula (aa) and a cation;

<4> The salt according to <3>, wherein the cation is an organic cation;

<5> The salt according to <3> or <4>, wherein the anion is represented by the formula (a2):

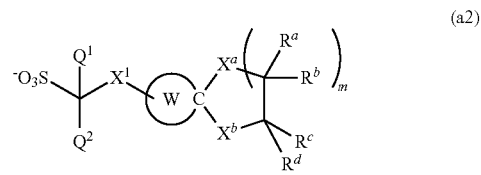

(a2)

wherein $X^a$, $X^b$, $R^a$, $R^b$, $R^c$, $R^d$ and m are the same as defined in <1>, W is the same as defined in <2>, $X^1$ represents a single bond or a C1-C17 saturated hydrocarbon group in which one or more —$CH_2$— can be replaced by —O— or —CO—, and $Q^1$ and $Q^2$ independently each represent a fluorine atom or a C1-C6 perfluoroalkyl group;

<6> The salt according to any one of <2> to <5>, wherein W is a ring represented by the formula (a1-1), (a1-2) or (a1-3):

(a1-1)

(a1-2)

(a1-3)

in which one or more —$CH_2$— can be replaced by —O—, —S—, —CO— or —$SO_2$—, and in which one or more hydrogen atoms can be replaced by a hydroxyl group, a C1-C12 alkyl group, a C1-C12 alkoxy group, a C3-C12 alicyclic hydrocarbon group or a C6-C10 aromatic hydrocarbon group;

<7> An acid generator comprising the salt according to any one of <1> to <6>;

<8> A photoresist composition comprising the acid generator according to <7> and a resin comprising a structural unit having an acid-labile group and being insoluble or poorly soluble in an aqueous alkali solution but becoming soluble in an aqueous alkali solution by the action of an acid;

<9> The photoresist composition according to <8>, wherein the photoresist composition further contains a basic compound;

<10> A process for producing a photoresist pattern comprising the following steps (1) to (5):
(1) a step of applying the photoresist composition according to <8> or <9> on a substrate,
(2) a step of forming a photoresist film by conducting drying,
(3) a step of exposing the photoresist film to radiation,
(4) a step of baking the exposed photoresist film, and (5) a step of developing the baked photoresist film with an alkaline developer, thereby forming a photoresist pattern.

DESCRIPTION OF PREFERRED EMBODIMENTS

The salt of the present invention has a divalent group represented by the formula (aa):

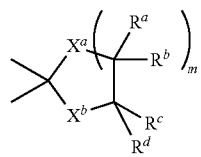

(aa)

wherein $X^a$ and $X^b$ independently each represent —O— or —S—, $R^a$, $R^b$, $R^c$ x and $R^d$ independently each represent a hydrogen atom, a C1-C4 alkyl group or a C1-C4 alkoxy group, and m represents 1 or 2 (hereinafter, simply referred to as the salt (aa)).

The salt (aa) has the divalent group represented by the formula (aa). The salt (aa) consists of an anion and a cation, and the anion may have the divalent group represented by the formula (aa), and the cation may have the divalent group represented by the formula (aa), and the anion and the cation may have the divalent groups represented by the formula (aa), respectively. The salt (aa) preferably has an anion having the divalent group represented by the formula (aa). In the formula (aa), $X^a$ and $X^b$ are preferably the same, and are more preferably —O—.

Examples of the C1-C4 alkyl group include a methyl group, an ethyl group, a propyl group, an isopropyl group, a butyl group, a sec-butyl group and a tert-butyl group. Examples of the C1-C4 alkoxy group include a methoxy group, an ethoxy group, a propoxy group, an isopropoxy group, a butoxy group, a sec-butoxy group and a tert-butoxy group $R^a$, $R^b$, $R^c$ and $R^d$ are preferably hydrogen atoms.

The salt (aa) preferably has a divalent group represented by the formula (a1):

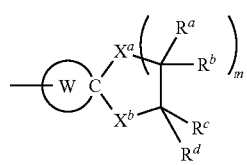

(a1)

wherein $X^a$, $X^b$, $R^a$, $R^b$, $R^c$, $R^d$ and m are the same as defined above, and W represents a C3-C36 saturated ring in which one or more —CH$_2$— can be replaced by —O—, —S—, —CO— or —SO$_2$—, and in which one or more hydrogen atoms can be replaced by a hydroxyl group, a C1-C12 alkyl group, a C1-C12 alkoxy group, a C3-C12 alicyclic hydrocarbon group or a C6-C10 aromatic hydrocarbon group.

Examples of the C3-C36 saturated ring include the following rings represented by the formulae (a1-1) to (a1-11):

 (a1-1)

 (a1-2)

 (a1-3)

 (a1-4)

 (a1-5)

 (a1-6)

 (a1-7)

 (a1-8)

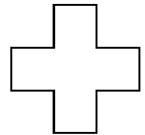 (a1-9)

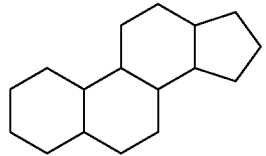 (a1-10)

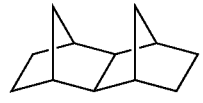 (a1-11)

in which one or more —CH$_2$— can be replaced by —O—, —S—, —CO— or —SO$_2$—, and in which one or more hydrogen atoms can be replaced by a hydroxyl group, a C1-C12 alkyl group, a C1-C12 alkoxy group, a C3-C12 alicyclic hydrocarbon group or a C6-C10 aromatic hydrocarbon group.

Examples of the C1-C12 alkyl group include a methyl group, an ethyl group, a propyl group, an isopropyl group, a butyl group, a sec-butyl group, a tert-butyl group, a pentyl group, a hexyl group, a heptyl group, a 2-ethylhexyl group, an octyl group, a nonyl group, a decyl group, an undecyl group and a dodecyl group. Examples of the C1-C12 alkoxy group include a methoxy group, an ethoxy group, a propoxy group, an isopropoxy group, a butoxy group, a sec-butoxy group, a tert-butoxy group, a pentyloxy group, a hexyloxy group, a heptyloxy group, a 2-ethylhexyloxy group, an octyloxy group, a nonyloxy group, a decyloxy group, an undecyloxy group and a dodecyloxy group.

Examples of the C3-C12 alicyclic hydrocarbon group include the following groups.

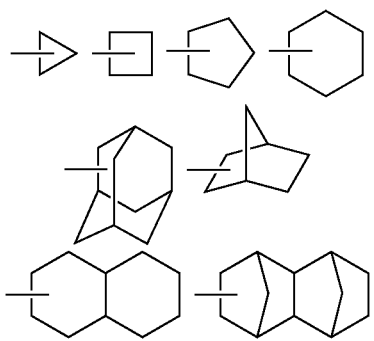

Examples of the C6-C10 aromatic hydrocarbon group include a phenyl group and a naphthyl group.

The salt (aa) is preferably a salt having an organic cation. The salt (aa) is preferably a salt consisting of an anion having the divalent group represented by the formula (aa) and a cation, and is more preferably a salt consisting of an anion having the divalent group represented by the formula (aa) and an organic cation.

The salt (aa) is preferably a salt containing an anion represented by the formula (a2):

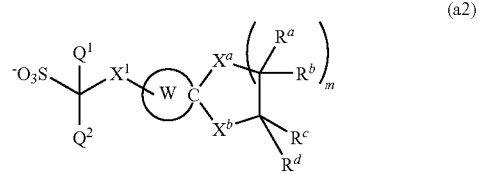

wherein $X^a$, $X^b$, $R^a$, $R^b$, $R^c$, $R^d$, m and W are the same as defined above, $X^1$ represents a single bond or a C1-C17 saturated hydrocarbon group in which one or more —CH$_2$— can be replaced by —O— or —CO—, and Q1 and Q2 independently each represent a fluorine atom or a C1-C6 perfluoroalkyl group.

Examples of the C1-C6 perfluoroalkyl group include a trifluoromethyl group, a pentafluoroethyl group, a heptafluoropropyl group, a nonafluorobutyl group, an undecafluoropentyl group and a tridecafluorohexyl group, and a trifluoromethyl group is preferable. $Q^1$ and $Q^2$ each independently preferably represent a fluorine atom or a trifluoromethyl group, and $Q^1$ and $Q^2$ are more preferably fluorine atoms.

Examples of the C1-C17 saturated hydrocarbon group include a C1-C17 alkylene group and a divalent group having an alicyclic hydrocarbon group. Examples of the alkylene group include a methylene group, an ethylene group, a trimethylene group, a tetramethylene group, a pentamethylene group, a hexamethylene group, a heptamethylene group, an octamethylene group, a nonamethylene group, a decamethylene group, an undecamethylene group, a dodecamethylene group, a tridecamethylene group, a tetradecamethylene group, a pentadecamethylene group, a hexadecamethylene group, a heptadecamethylene group, an isopropylene group, a sec-bytylene group and a tert-butylene group. Examples of the divalent group having an alicyclic hydrocarbon group include the following groups represented by the formulae $(X^1-A)$ to $(X^1—C)$:

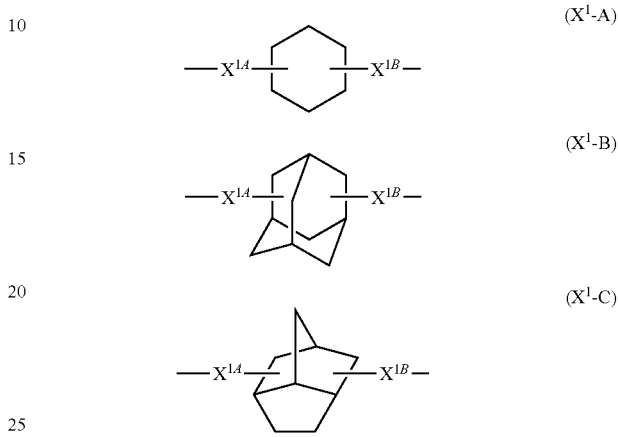

wherein $X^{1A}$ and $X^{1B}$ independently each represent a C1-C6 alkylene group which can have one or more substituents, with the proviso that total carbon number of the group represented by the formula $(X^1-A)$, $(X^1—B)$ or $(X^1—C)$ is 1 to 17.

Examples of $X^1$ include the following groups in which * is a binding position to —CQ$^1$Q$^2$-.

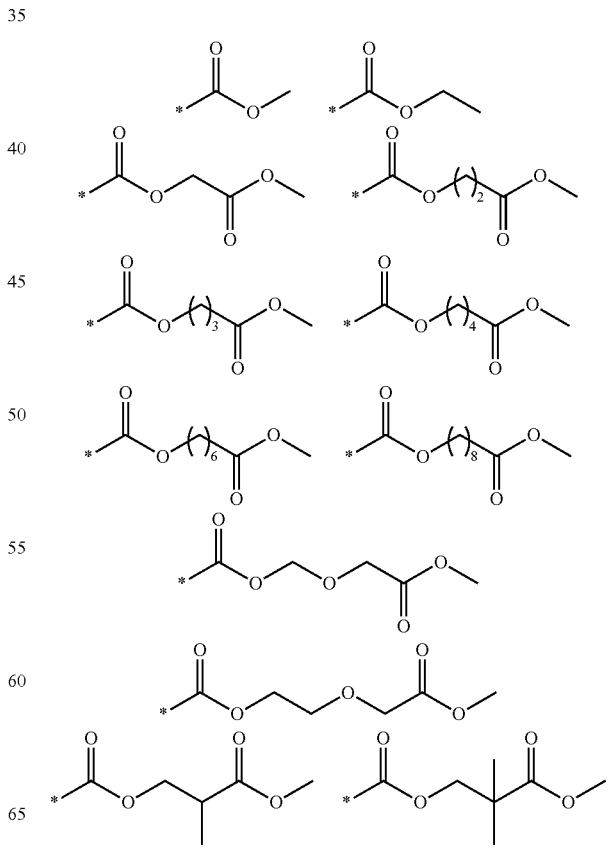

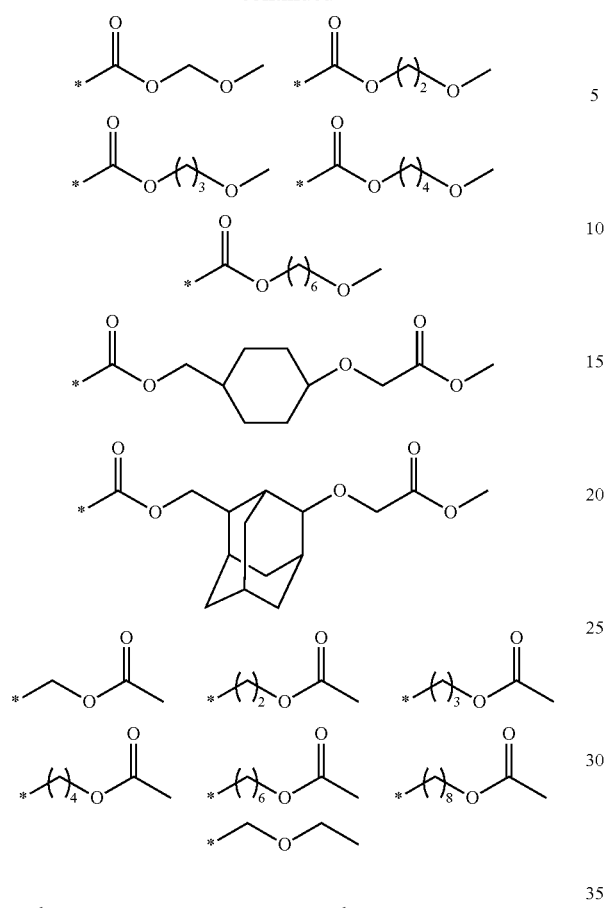
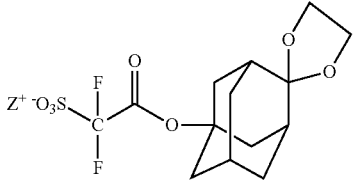
(a1-1-2)
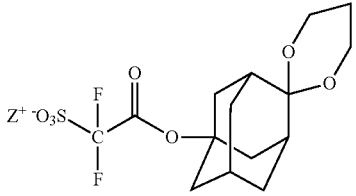
(a1-1-2)
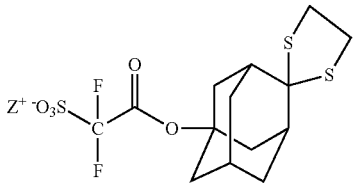
(a1-1-3)
$X^1$ is preferably *—CO—O—$X^{a1}$— wherein * is a binding position to —$CQ^1Q^2$- and $X^{a1}$ represents a single bond or a C1-C15 alkylene group in which one or more —$CH_2$— can be replaced by —O— or —CO—.
Examples of *—CO—O—$X^{a1}$— include the followings.
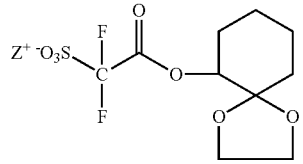
(a1-2-1)
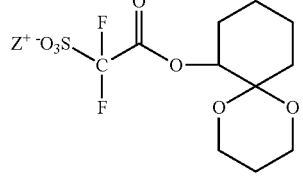
(a1-2-2)
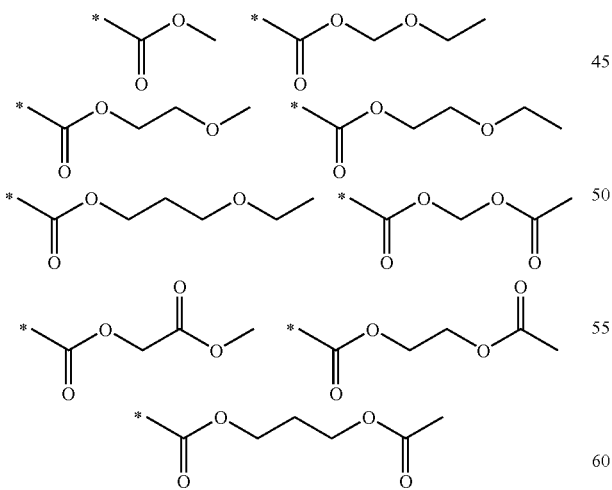
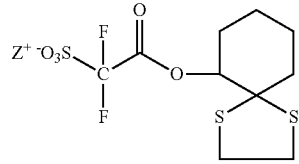
(a1-2-3)
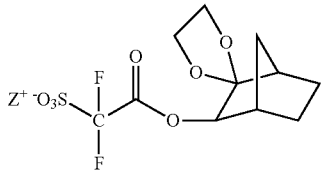
(a1-3-1)
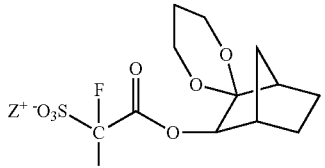
(a1-3-2)
Among them, *—CO—O— is preferable.
The salt (aa) is preferably a salt represented by the formula (a1-1-1), (a1-1-2), (a1-1-3), (a1-2-1), (a1-2-2), (a1-2-3), (a1-3-1), (a1-3-2) or (a1-3-3):

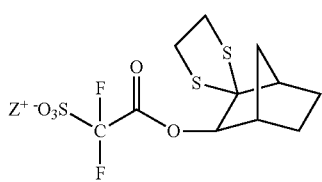

(a1-3-3)

wherein $Z^+$ represents a cation.

Examples of the anion represented by the formula (a2) include the anion represented by the formula (a2) wherein $X^1$ is *—CO—O—$X^{10}$—, the anion represented by the formula (a2) wherein $X^1$ is *—CO—O—$X^{11}$—CO—O—, the anion represented by the formula (a2) wherein $X^1$ is *—$X^{10}$—O—CO—, and the anion represented by the formula (a2) wherein $X^1$ is *—$X^{12}$—O—$X^{13}$—, and in the above-mentioned formulae, * is a binding position to —$CQ^1Q^2$-, $X^{10}$ is a single bond or a C1-C15 saturated hydrocarbon group, $X^{11}$ is a single bond or a C1-C13 saturated hydrocarbon group, $X^{12}$ is a single bond or a C1-C16 saturated hydrocarbon group, $X^{13}$ is a single bond or a C1-C16 saturated hydrocarbon group, with the proviso that total carbon numbers of $X^{12}$ and $X^{13}$ is 1 to 16.

Examples of the anion represented by the formula (a2) include the followings.

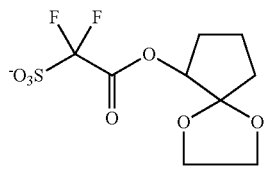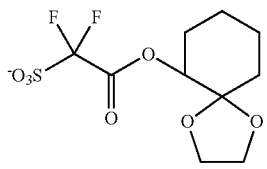
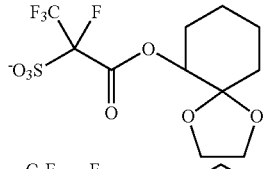
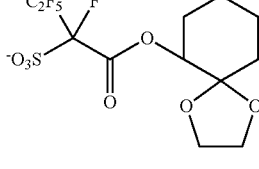
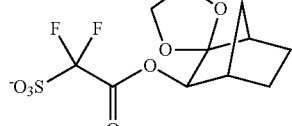
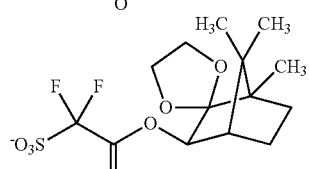
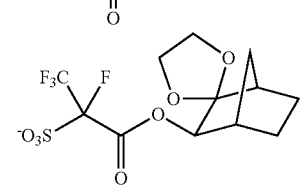
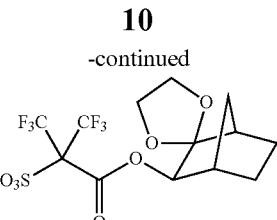
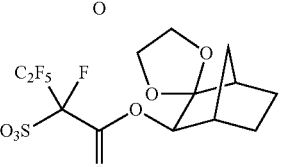
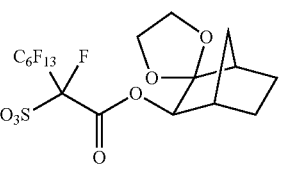
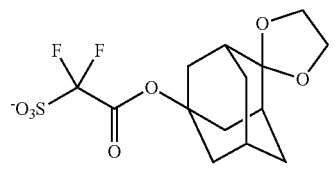
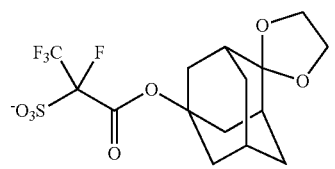
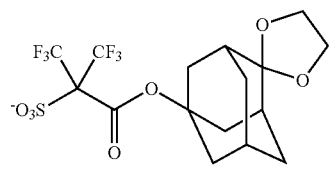
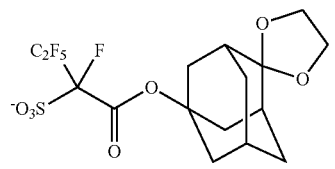
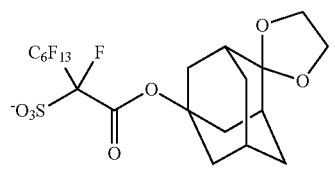
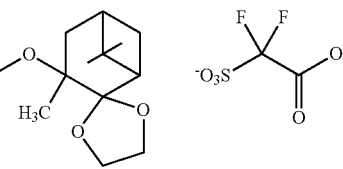
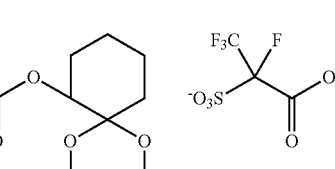

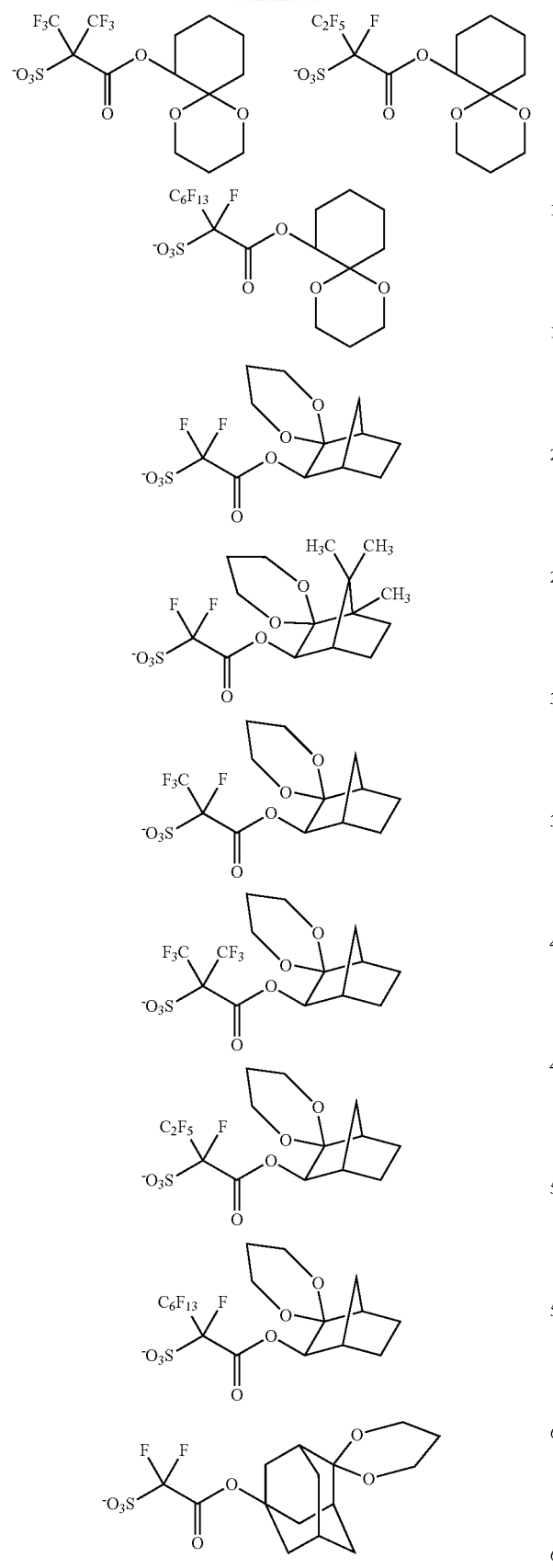
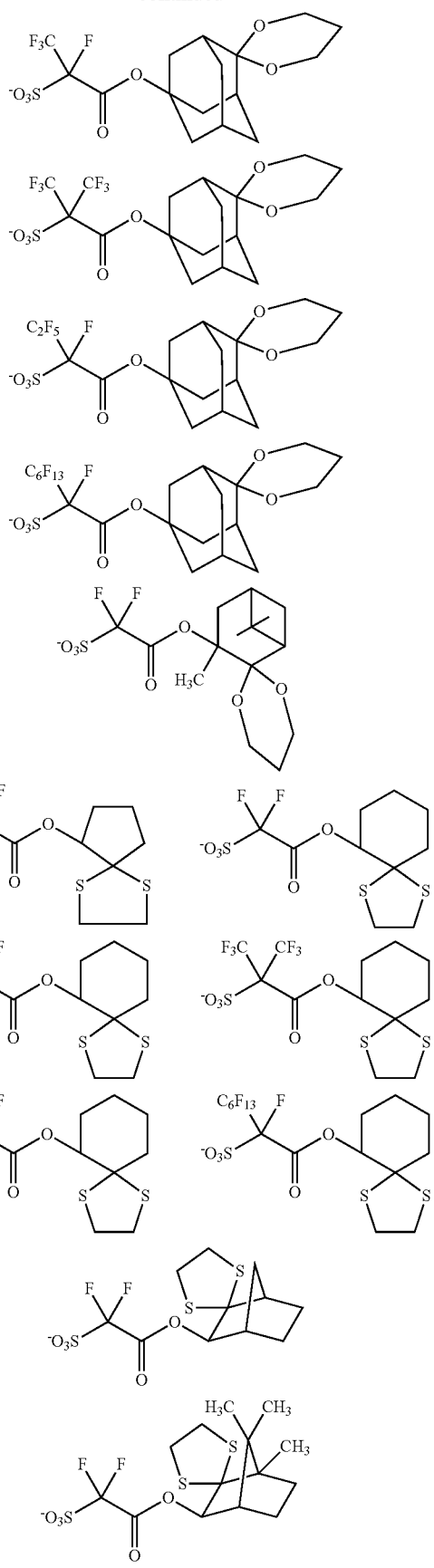

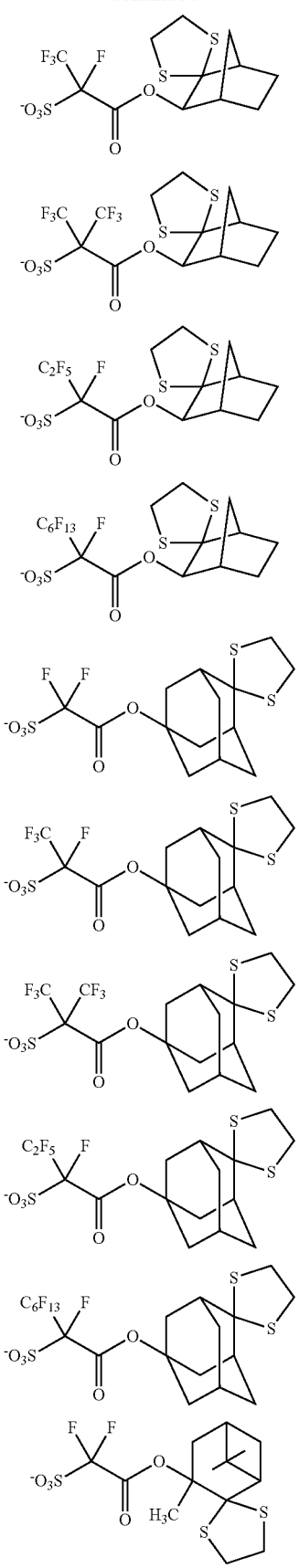
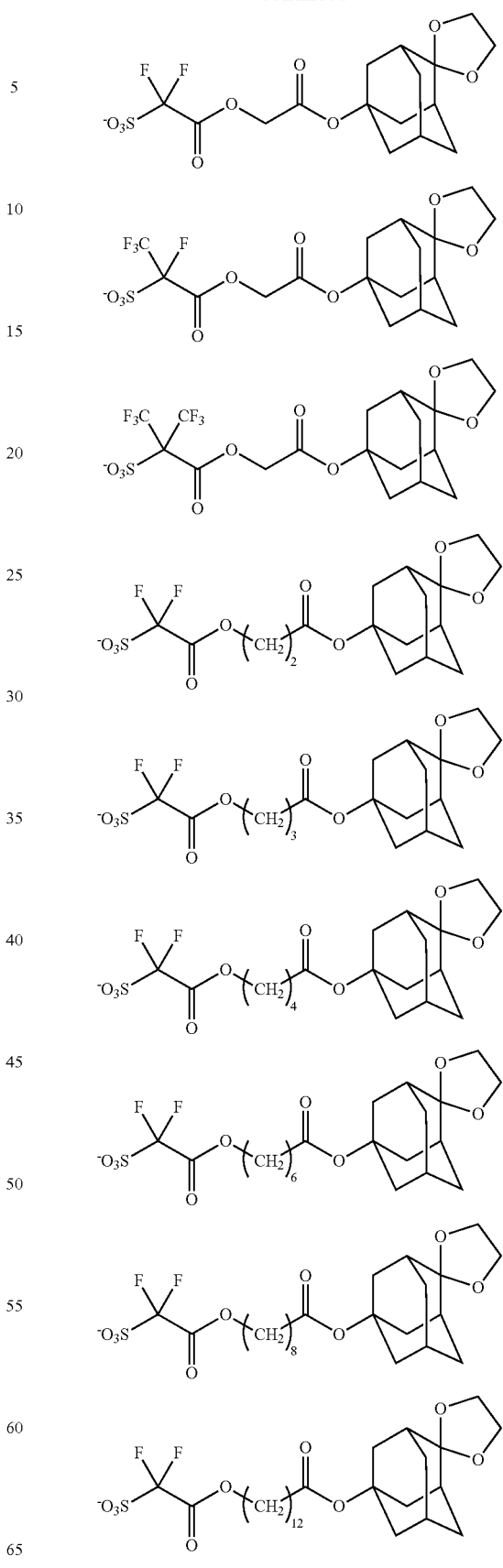

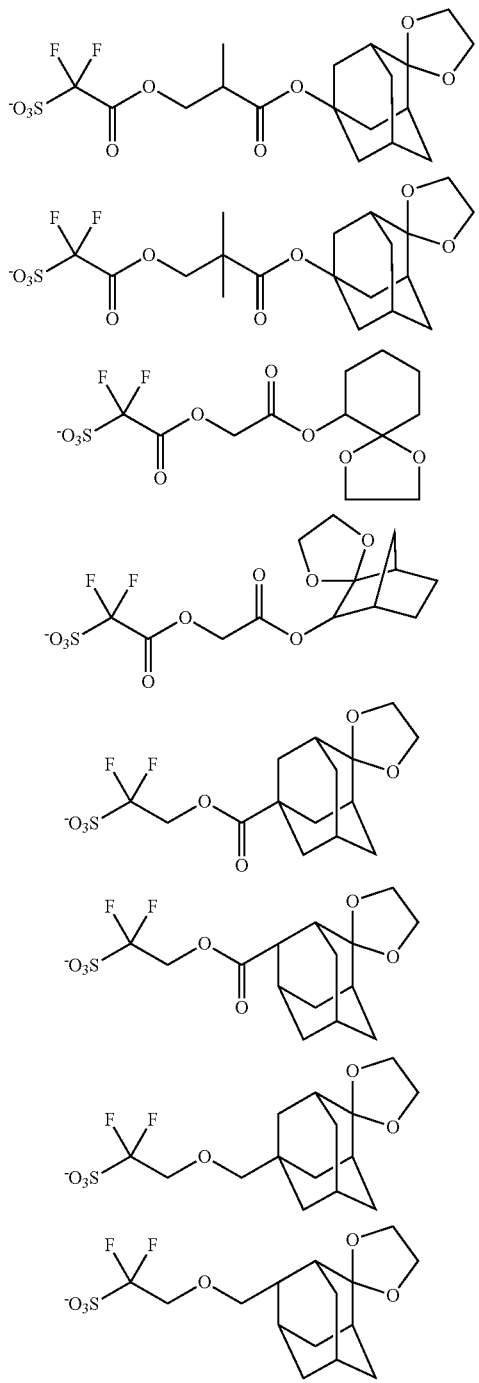

The cation of the salt (aa) is preferably an organic cation, and examples thereof include cations represented by the formulae (IXa), (IXb), (IXc) and (IXd), and a cation represented by the formula (IXa) is preferable.

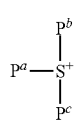
(IXa)

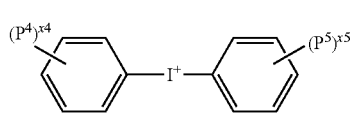
(IXb)

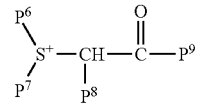
(IXc)

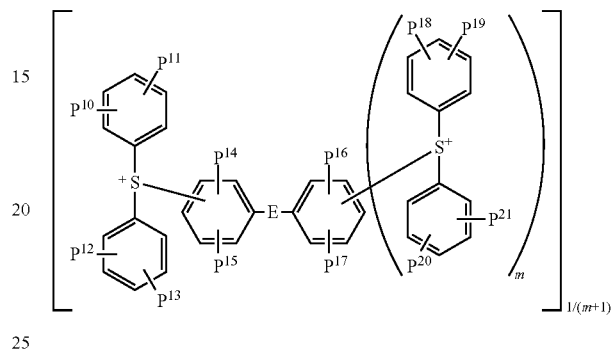
(IXd)

wherein $P^a$, $P^b$ and $P^c$ each independently represent a C1-C30 alkyl group which can have one or more substituents selected from the group consisting of a hydroxyl group, a C1-C12 alkoxy group and a C3-C12 alicyclic hydrocarbon group, a C3-C30 alicyclic hydrocarbon group which can have one or more substituents selected from the group consisting of a hydroxyl group, a C1-C12 alkyl group and a C1-C12 alkoxy group, or a C6-C20 aromatic hydrocarbon group which can have one or more substituents, and $P^a$ and $P^b$ can be bonded each other to form a ring, $P^4$ and $P^5$ are independently in each occurrence a hydrogen atom, a hydroxyl group, a C1-C12 alkyl group or a C1-C12 alkoxy group, x4 and x5 independently represents an integer of 1 to 5, and $P^6$ and $P^7$ each independently represent a C1-C12 alkyl group or a C3-C12 cycloalkyl group, or $P^6$ and $P^7$ are bonded to form a C3-C12 divalent acyclic hydrocarbon group which forms a ring together with the adjacent $S^+$, and $P^8$ represents a hydrogen atom, $P^9$ represents a C1-C12 alkyl group, a C3-C12 cycloalkyl group or a C6-C20 aromatic group which may be substituted, or $P^8$ and $P^9$ are bonded each other to form a C1-C10 divalent acyclic hydrocarbon group which forms a 2-oxocycloalkyl group together with the adjacent —CHCO—, and $P^{10}$, $P^{11}$, $P^{12}$, $P^{13}$, $P^{14}$, $P^{15}$, $P^{16}$, $P^{17}$, $P^{18}$, $P^{19}$, $P^{20}$ and $P^{21}$ each independently represent a hydrogen atom, a hydroxyl group, a C1-C12 alkyl group or a C1-C12 alkoxy group, E represents a sulfur atom or an oxygen atom and m represents 0 or 1.

Examples of the alkyl group include a methyl group, an ethyl group, a propyl group, an isopropyl group, a butyl group, a sec-butyl group, a tert-butyl group, a pentyl group, a hexyl group, a heptyl group, an octyl group, a 2-ethylhexyl group, a nonyl group and a decyl group.

Examples of the alicyclic hydrocarbon group include a cyclopropyl group, a cyclobutyl group, a cyclopentyl group, a cyclohexyl group, a cycloheptyl group, a cyclooctyl group, a cyclononyl group, a cyclodecyl group, a norbornyl group, a 1-adamantyl group, a 2-adamantyl group and an isobornyl group.

Examples of the aromatic hydrocarbon group include a phenyl group, a naphthyl group and an anthryl group.

The ring formed by bonding $P^a$ and $P^b$ each other may be a saturated ring or an aromatic ring.

Examples of the C3-C12 divalent acyclic hydrocarbon group formed by bonding $P^6$ and $P^7$ include a trimethylene group, a tetramethylene group and a pentamethylene group. Examples of the ring group formed together with the adjacent $S^+$ and the divalent acyclic hydrocarbon group include the followings, and a tetrahydrothiophenium group is preferable.

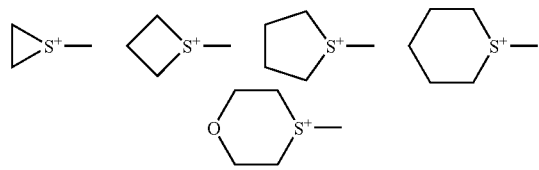

Examples of the substituent of the C6-C20 aromatic hydrocarbon group represented by $P^9$ include a C1-C12 alkyl group.

Examples of the ring formed by bonding $P^8$ and $P^9$ include the followings.

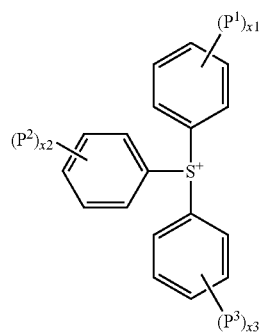

Among the cation represented by the formula (IXa), a cation represented by the formula (IXaa), (IXab) or (IXac) is preferable.

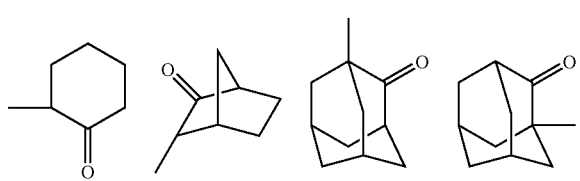

(IXaa)

wherein $P^1$, $P^2$ and $P^3$ independently each represent a hydrogen atom, a hydroxyl group, a C1-C12 alkyl group, a C1-C12 alkoxy group, or a C4-C36 alicyclic hydrocarbon group, and any two of $P^1$, $P^2$ and $P^3$ can be bonded each other to form a ring, and one or more hydrogen atoms in the alicyclic hydrocarbon group can be replaced by a halogen atom, a hydroxyl group, a C1-C12 alkyl group, a C1-C12 alkoxy group, a C6-C12 aryl group, a C7-C12 aralkyl group, a glycidyloxy group or a C2-C4 acyl group, x1, x2 and x3 independently each represents an integer of 1 to 5,

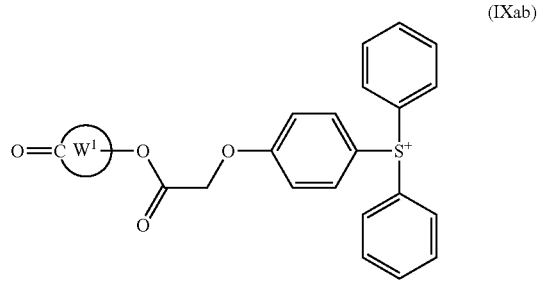

(IXab)

wherein $W^1$ is the same as W,

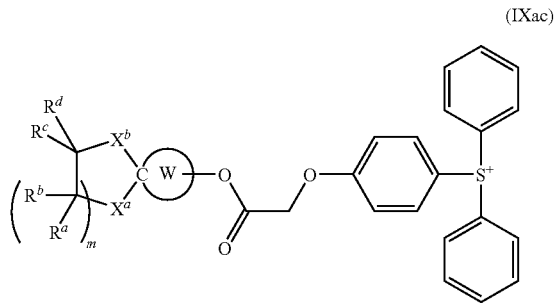

(IXac)

wherein $X^a$, $X^b$, $R^a$, $R^b$, $R^c$, $R^d$, m and W are the same as defined above.

The ring formed by bonding any two of $P^1$, $P^2$ and $P^3$ each other may be a saturated ring or an aromatic ring.

Preferred examples of the alicyclic hydrocarbon group are 2-alkyl-2-adamantyl group, 1-(1-adamantyl)-1-alkyl group and an isobornyl group.

Examples of the cation represented by the formula (IXaa) include the followings.

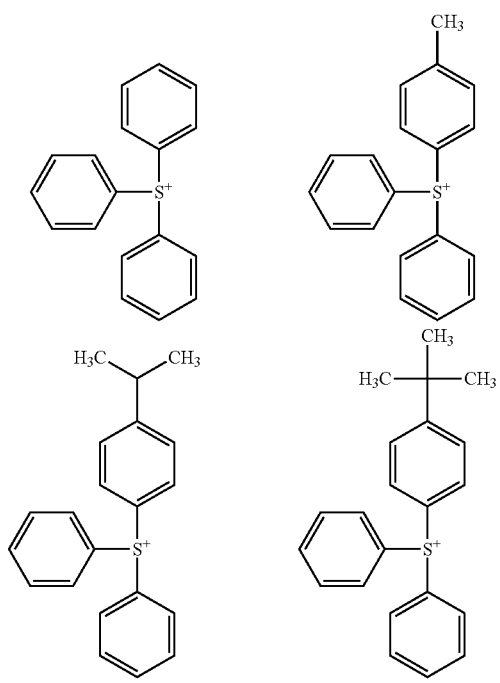

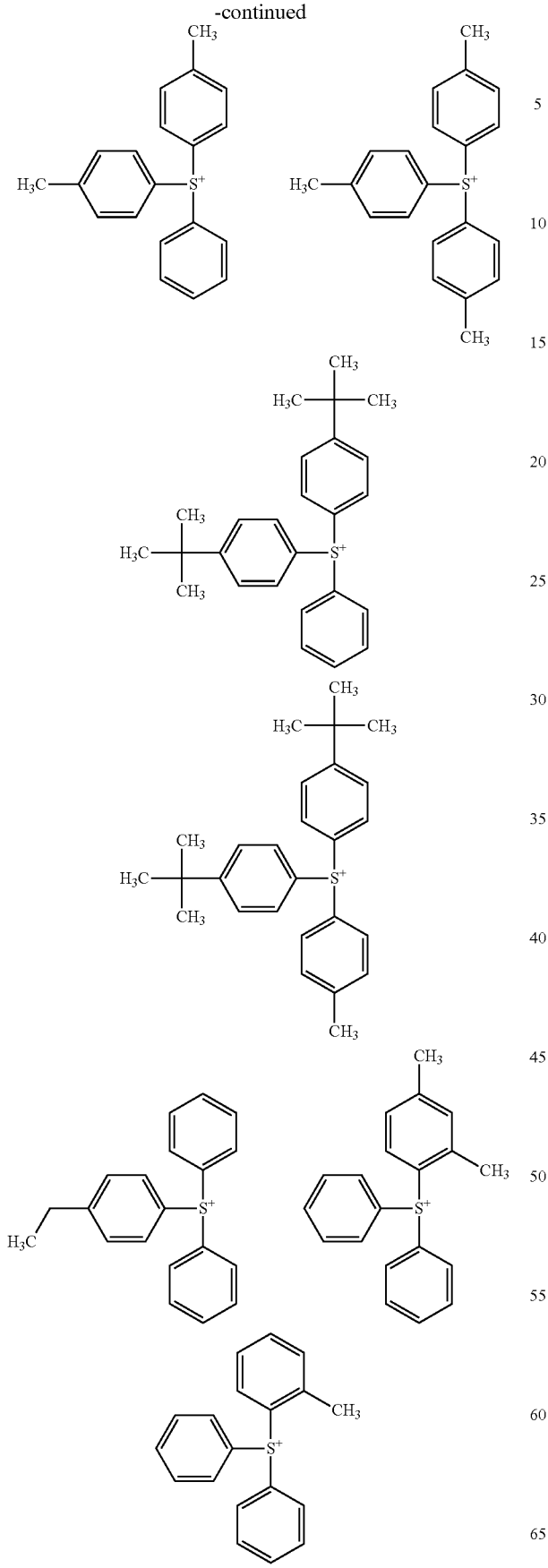
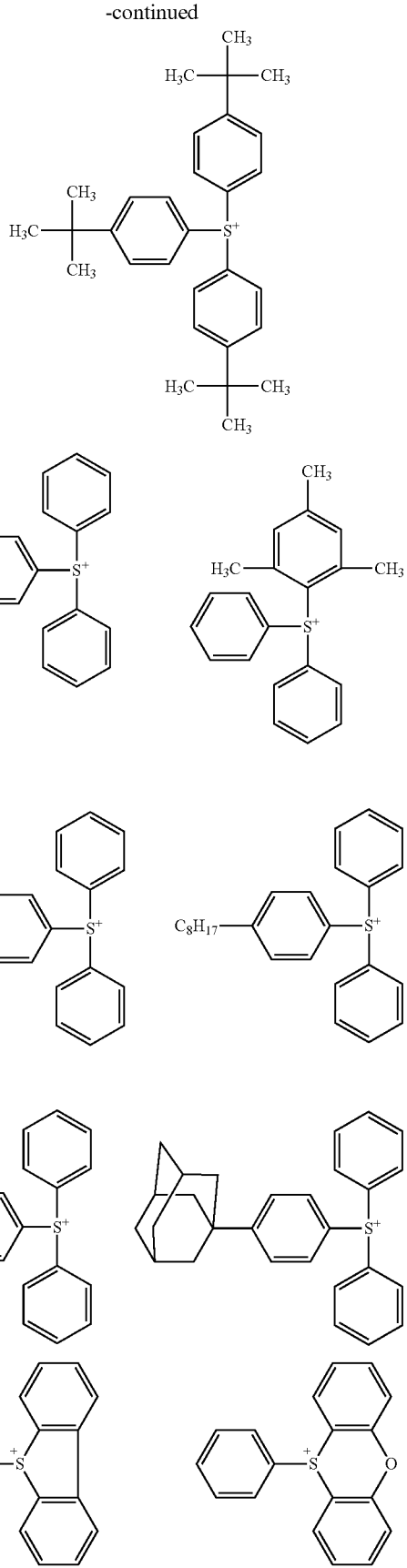

-continued
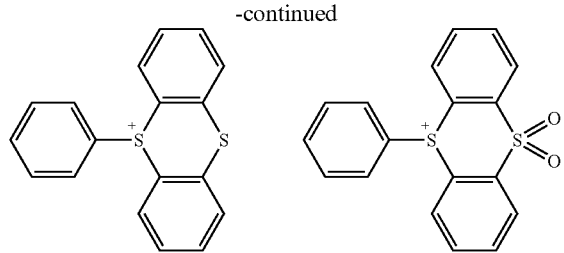
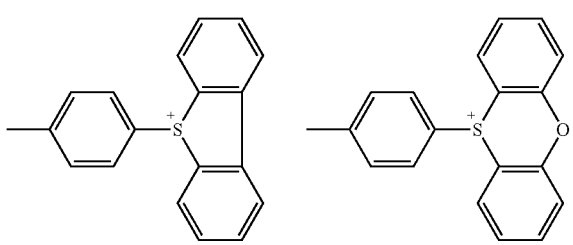
Examples of the cation represented by the formula (IXab) include the followings.
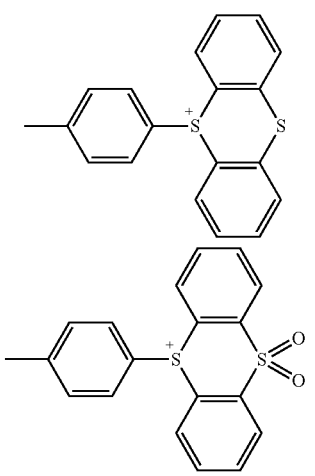
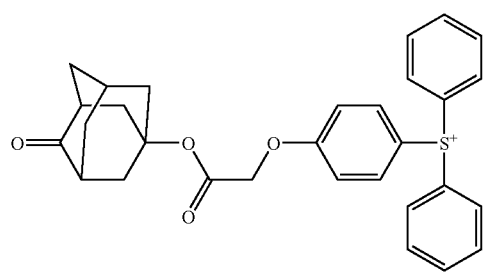 [SMILES: O=C(COc1ccc([S+](c2ccccc2)c2ccccc2)cc1)OC12CC3CC(C1)C(=O)C(C3)C2]
Examples of the cation represented by the formula (IXac) include the followings.
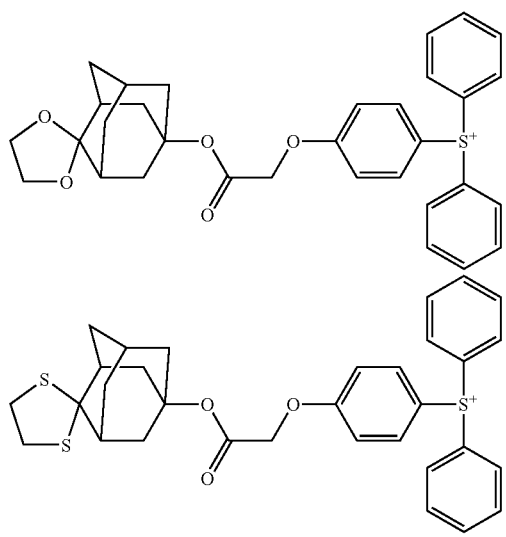
Examples of the cation represented by the formula (IXb) include the followings.
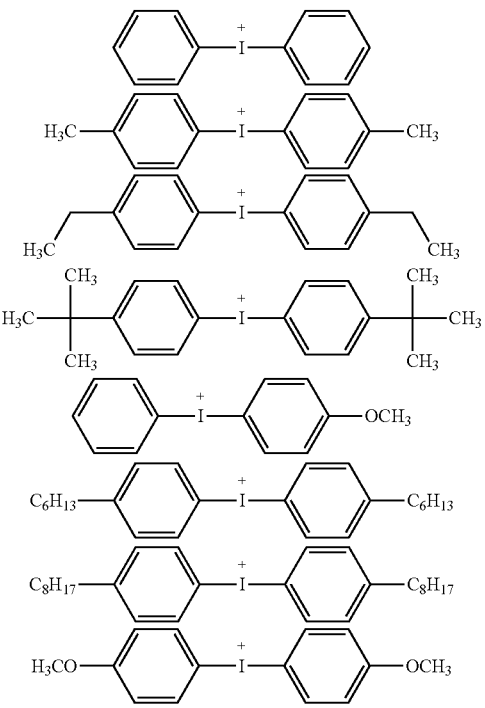
Examples of the cation represented by the formula (IXc) include the following.
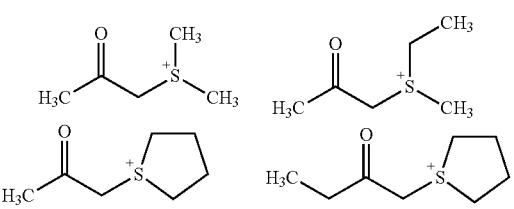

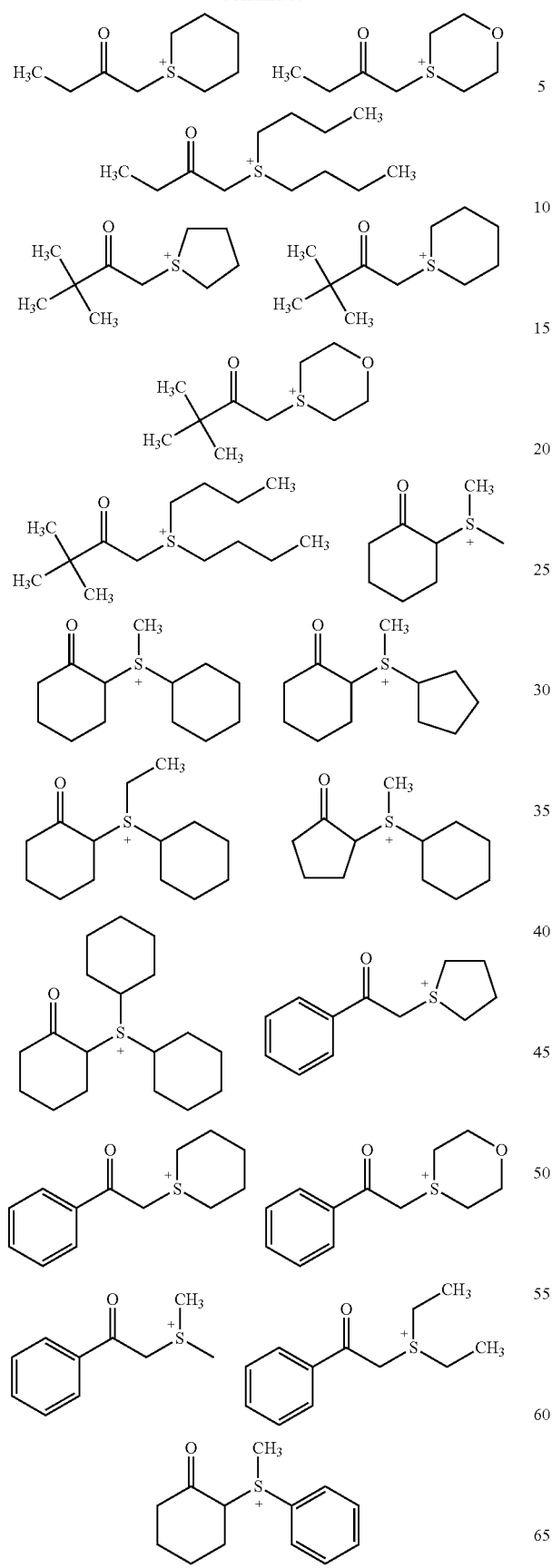
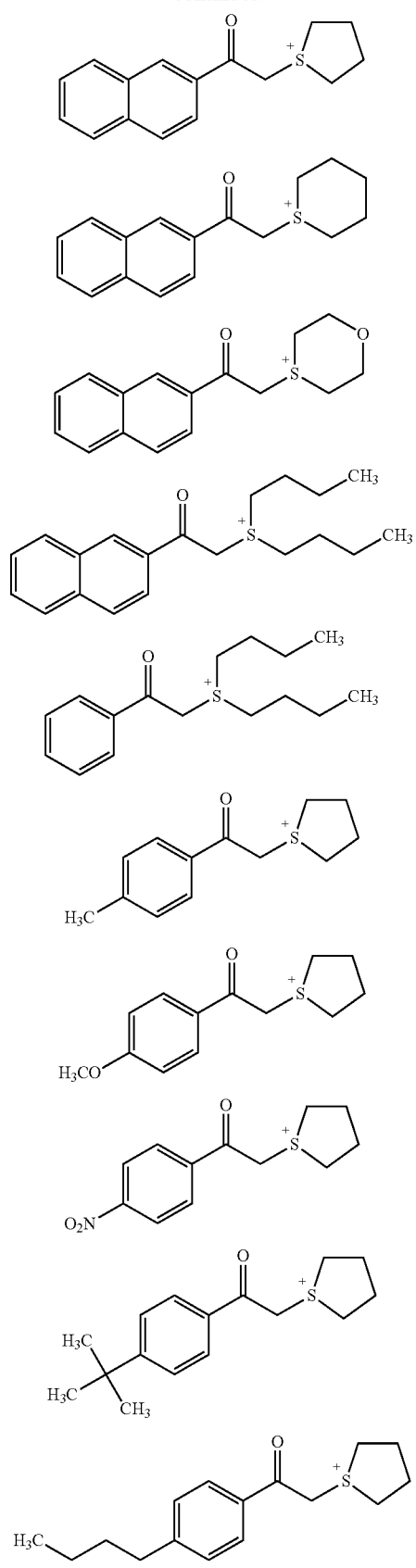

-continued
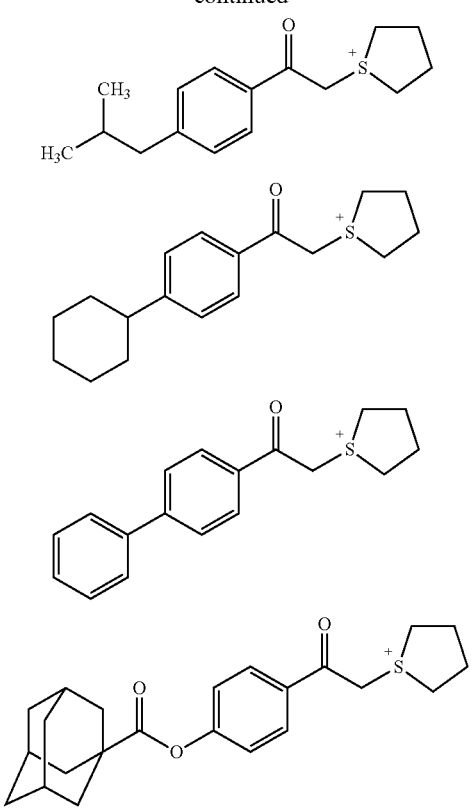
Examples of the cation represented by the formula (IXd) include the following.
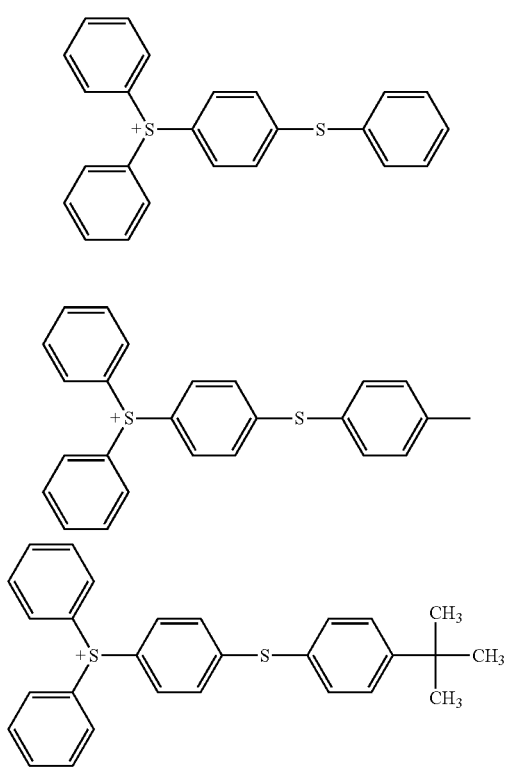
-continued
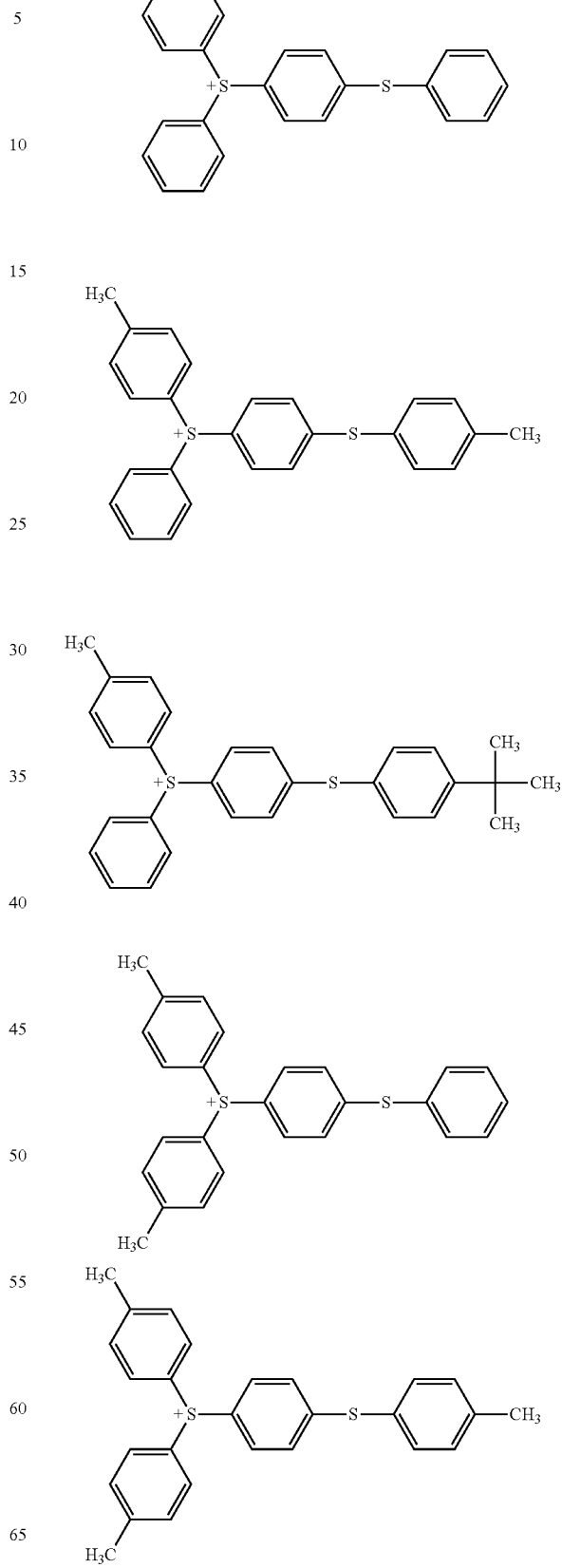

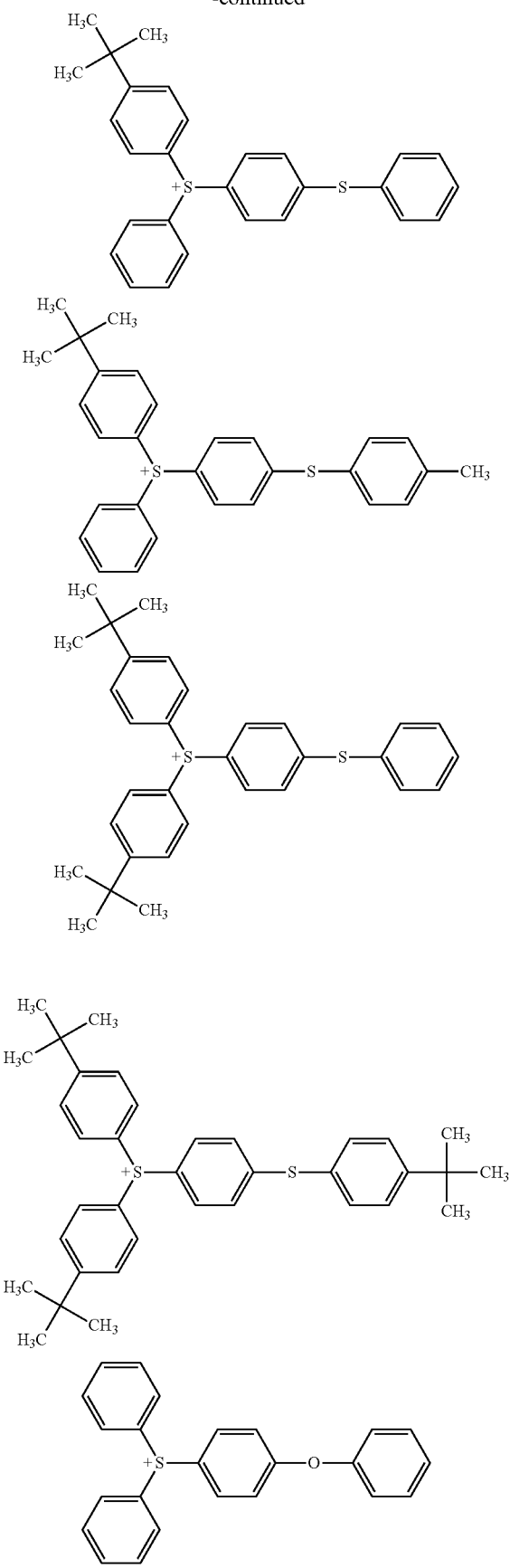

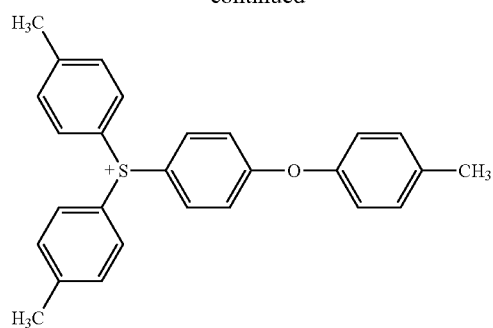
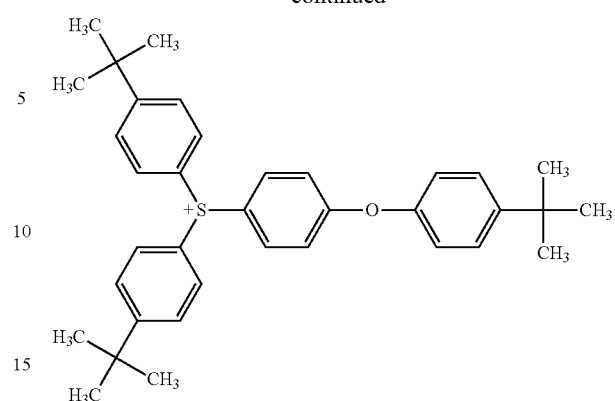
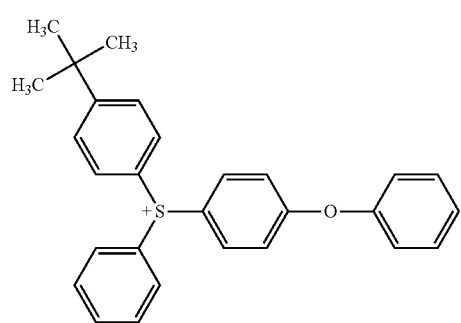
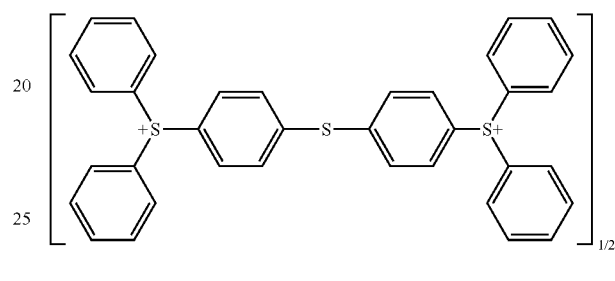
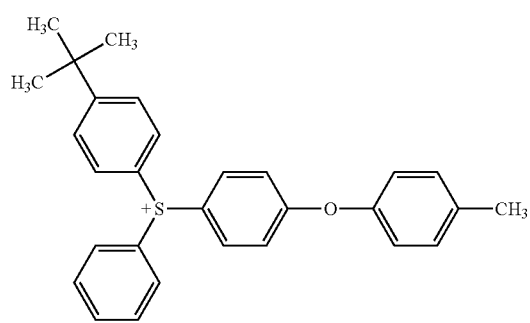
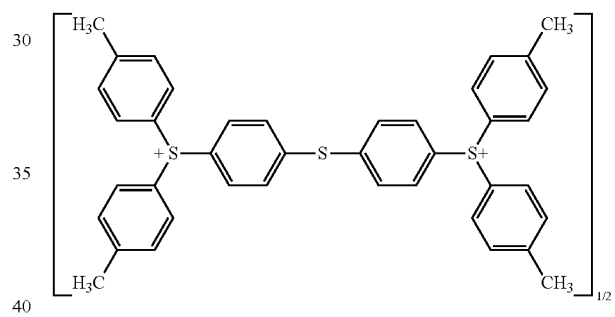
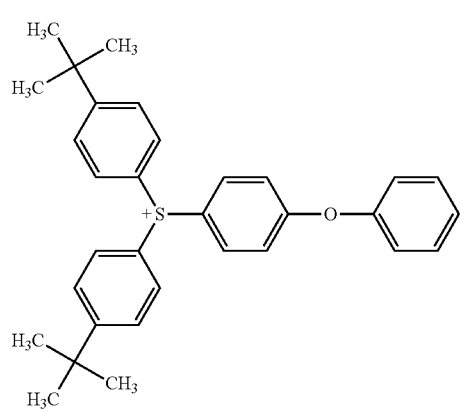
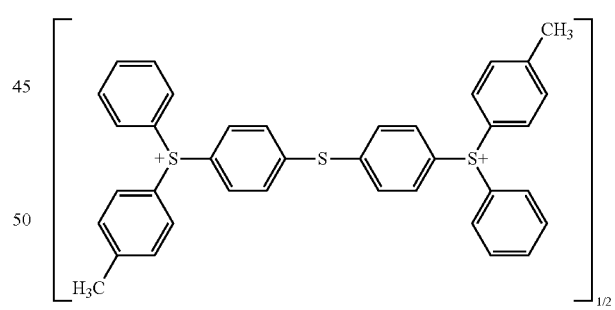
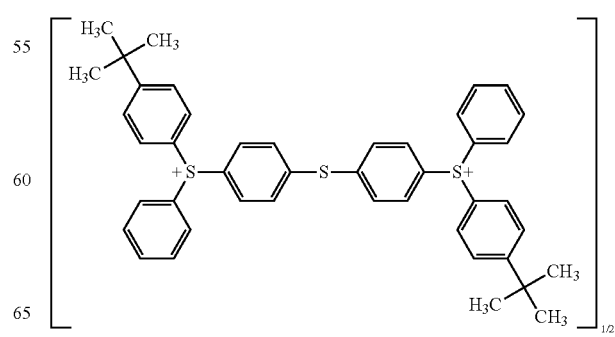

-continued
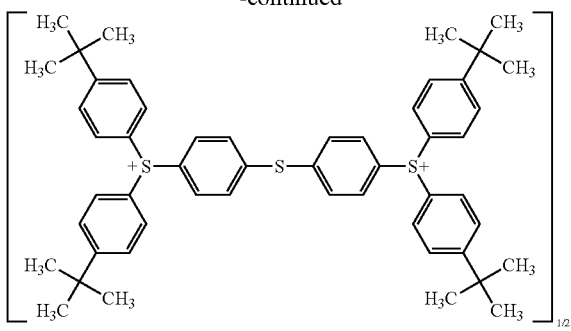
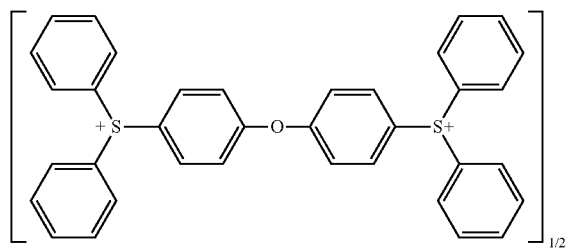
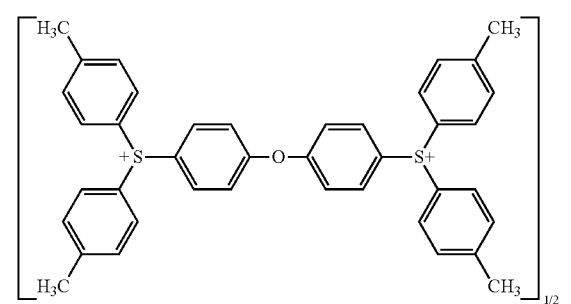
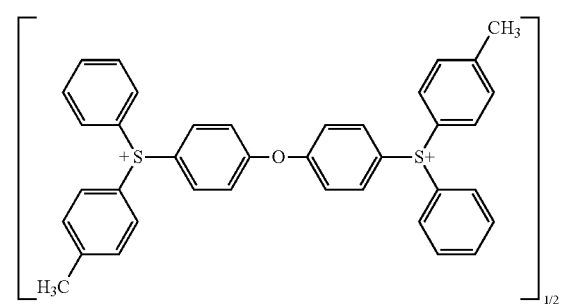
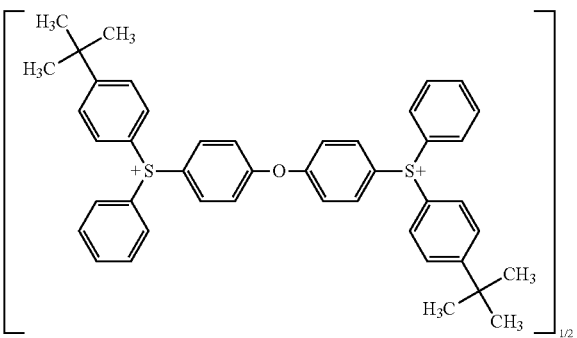
-continued
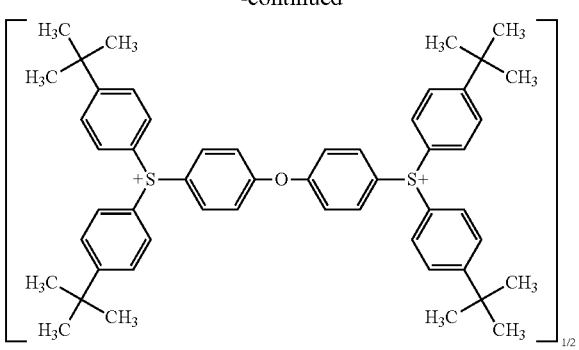
Among them, a triarylsulfonium cation is preferable.
Examples of the salt (aa) include a salt consisting of any one of the above-mentioned anion and any one of the above-mentioned cation.
Examples of the salt (aa) include the followings.
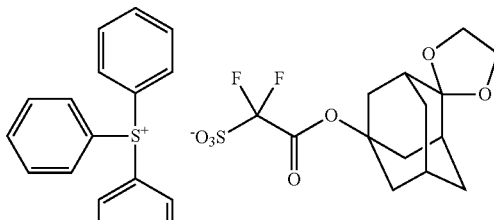
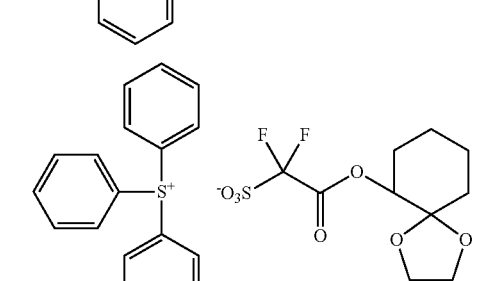
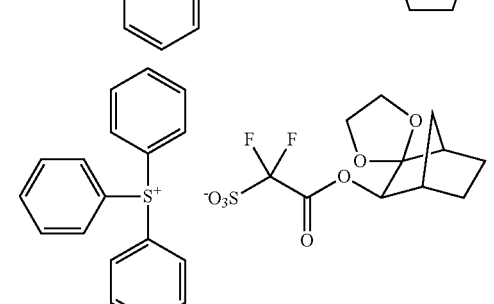
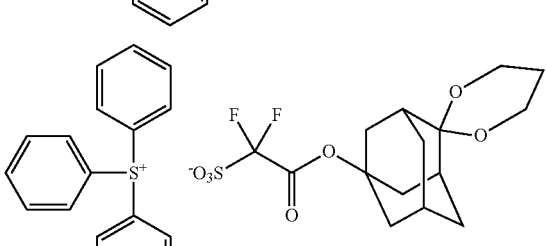

-continued

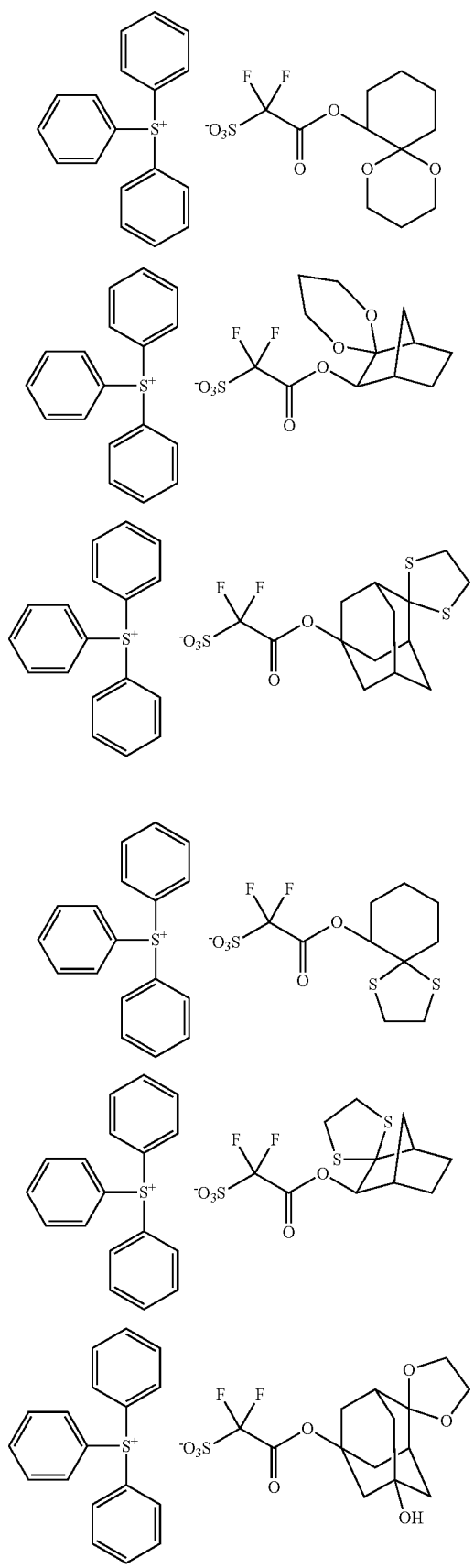

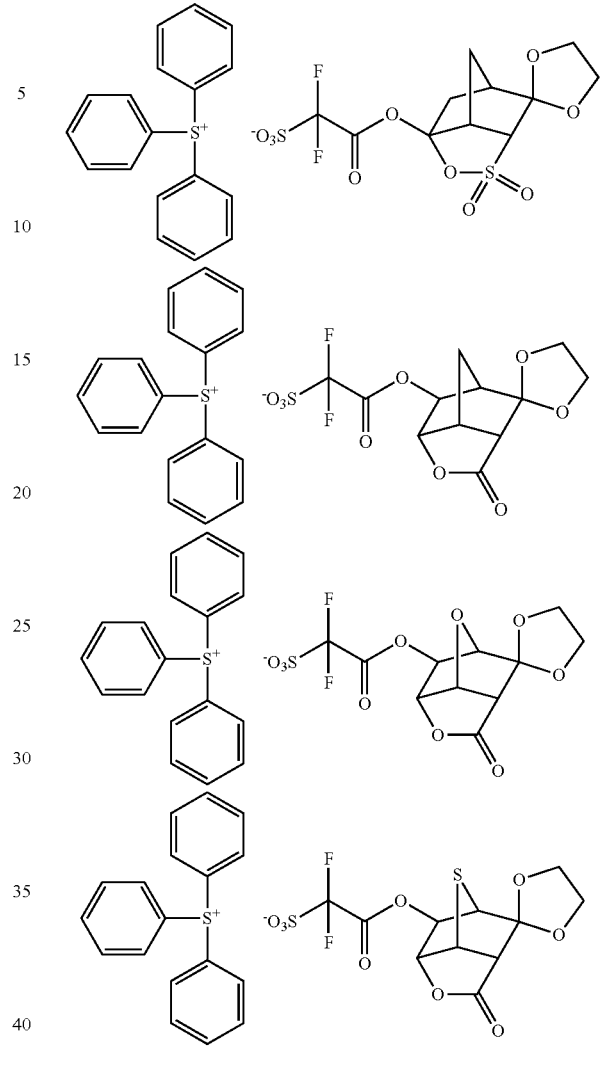

The salt (aa) may be a salt comprising a cation having the divalent group represented by the formula (aa). Examples thereof include a salt having a cation represented by the formula (IXac).

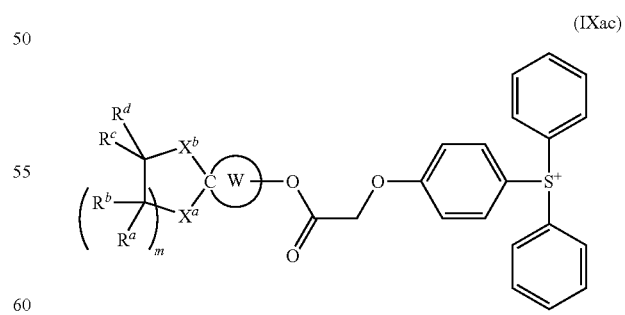

wherein $X^a$, $X^b$, $R^a$, $R^c$, $R^d$, m and W are the same as defined above.

Examples of anion of the salt having a cation represented by the formula (IXac) include the above-mentioned anion having the divalent group represented by the formula (aa) and the known anions described in JP 2006-257078A, JP2007-224008A and JP2004-4561 A.

Examples of the salt having a cation represented by the formula (IXac) include the followings.

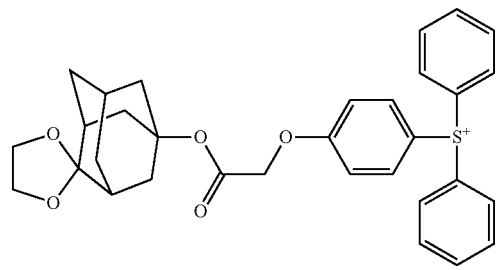
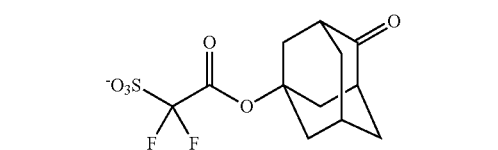
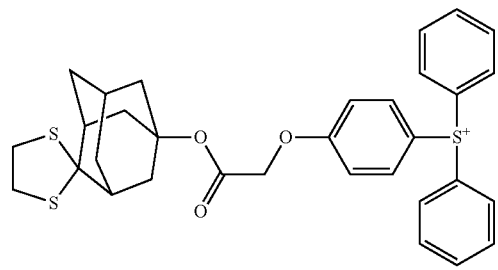
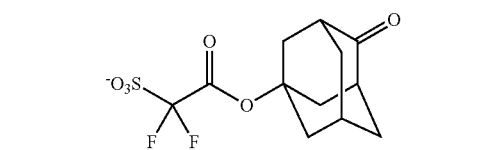
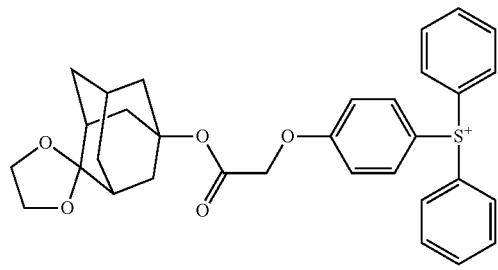
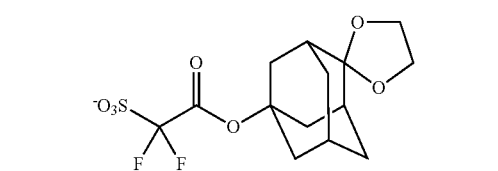
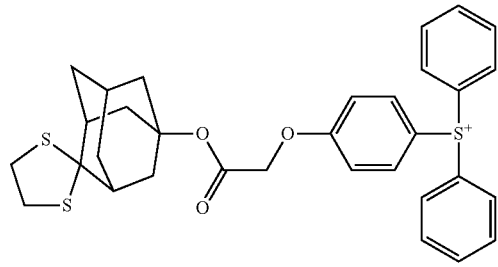

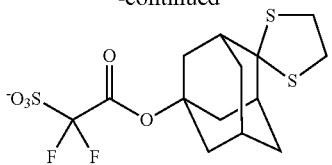
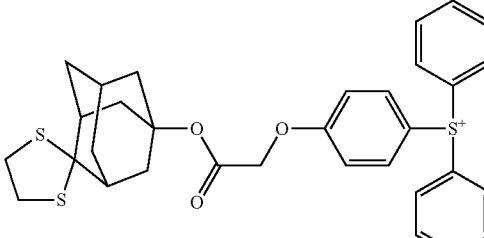
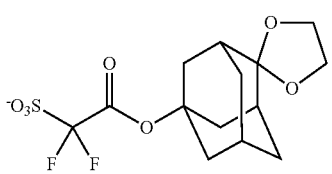
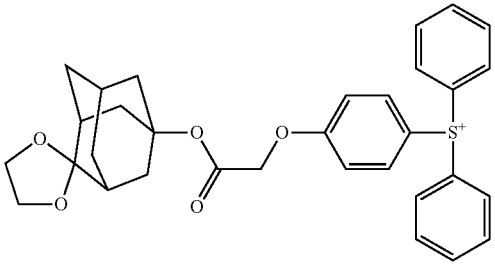
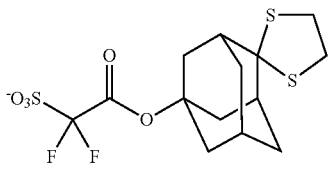

The process for producing the salt (aa) will be illustrated.

The salt (aa) having an anion having the divalent group represented by the formula (aa) can be produced by reacting a salt represented by the formula (a4):

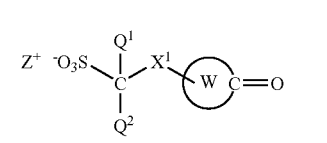

(a4)

wherein $Z^+$, $Q^1$, $Q^2$, $X^1$ and W are the same as defined above, with a diol compound such as ethylene glycol and 1,3-propanediol, or a dithiol compound such as 1,2-ethanedithiol, in the presence of an acid catalyst. The salt represented by the formula (a4) is disclosed in JP 2007-224008 A. The above-mentioned reaction is usually conducted in an aprotic solvent at about 20 to 200° C., preferably at about 50 to 150° C. with stirring. As the acid catalyst, an organic acid such as p-toluenesulfonic acid is preferable. Examples of the aprotic solvent include dichloroethane, toluene, ethylbenzene, monochlorobenzene, acetonitrile and N,N-dimethylformamide.

The reaction can be carried out in the presence of a dehydrating agent, and examples of the dehydrating agent include 1,1'-carbonyldiimidazole, N,N'-dicyclohexylcarbodiimide, 1-alkyl-2-halopyridinium salt, bis(2-oxo-3-oxazolidinyl)phosphinic acid chloride, 1-ethyl-3-(3-dimethylaminopropyl)carbodiimide hydrochloric acid salt, di-2-pyridyl carbonate, and di-2-pyridylthiono carbonate. The reaction using the acid catalyst may preferably be carried out with dehydration, for example, by Dean and Stark method as the reaction time tends to be shortened.

The salt (aa) having a cation having the divalent group represented by the formula (aa) can be produced by reacting a salt represented by the formula (a5):

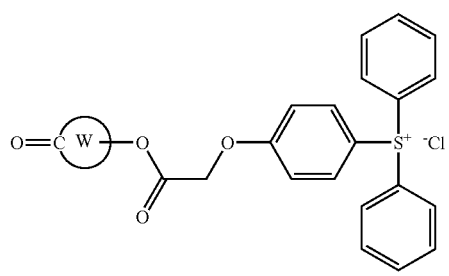

(a5)

wherein W is the same as defined above, with a diol compound such as ethylene glycol and 1,3-propanediol, or a dithiol compound such as 1,2-ethanedithiol, in the presence of an acid catalyst, followed by reacting the obtained product with a sodium salt according to the known methods described in JP 2007-224008A. The above-mentioned reaction is usually conducted in an aprotic solvent at about 20 to 200° C., preferably at about 50 to 150° C. with stirring. As the acid catalyst, an organic acid such as p-toluenesulfonic acid is preferable. Examples of the aprotic solvent include the same as described above. The salt represented by the formula (a5) can be produced by reacting a compound represented by the formula (a5-1) with a salt represented by the formula (a5-2) in the presence of a catalyst such as potassium carbonate and potassium iodide in a solvent such as N,N-dimethylformamide.

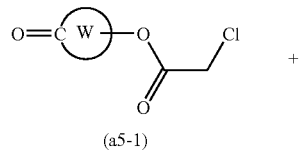

(a5-1)

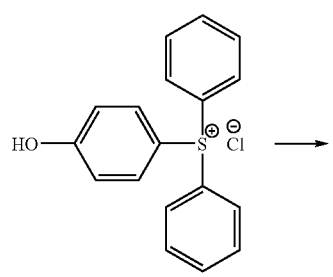

(a5-2)

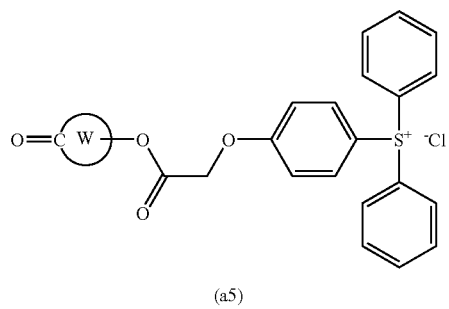

(a5)

The salt (aa) having a cation having the divalent group represented by the formula (aa) and an anion having the divalent group represented by the formula (aa) can be produced by reacting a salt represented by the formula (a6):

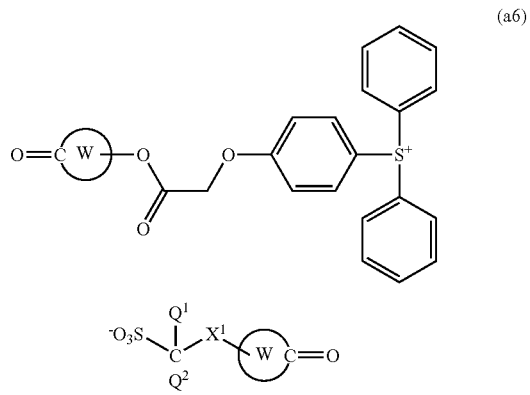

(a6)

wherein W, $Q^1$, $Q^2$ and $X^1$ are the same as defined above, with a diol compound such as ethylene glycol and 1,3-propanediol, or a dithiol compound such as 1,2-ethanedithiol, in the presence of an acid catalyst, followed by reacting the obtained product with a sodium salt according to the known methods described in JP 2007-224008 A. The above-mentioned reaction is usually conducted in an aprotic solvent at about 20 to 200° C., preferably at about 50 to 150° C. with stirring. As the acid catalyst, an organic acid such as p-toluenesulfonic acid is preferable. Examples of the aprotic solvent include the same as described above. The salt represented by the formula (a6) can be produced by reacting a salt represented by the formula (a5) with a salt represented by the formula (a6-1) in a solvent such as chloroform.

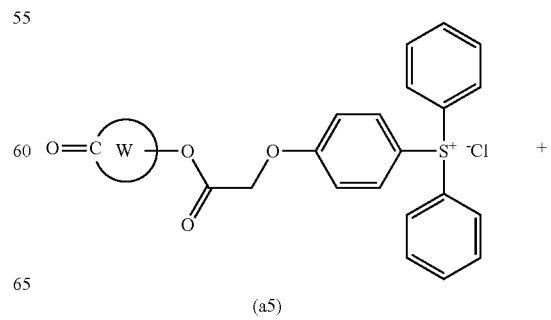

(a5)

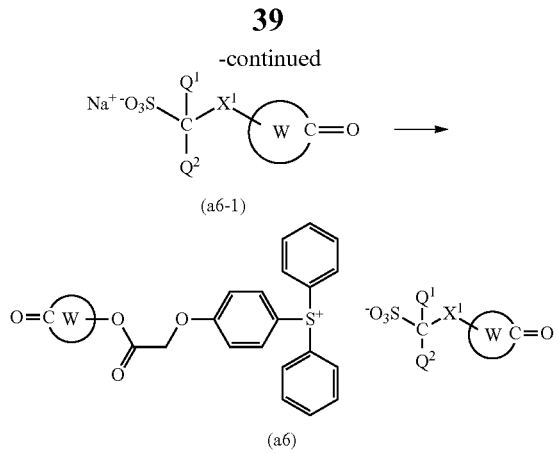

(a6-1)

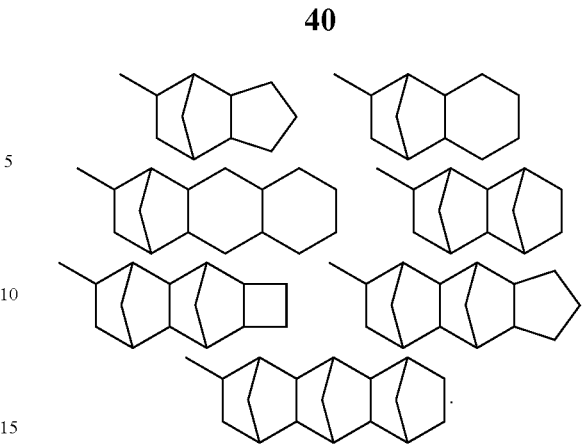

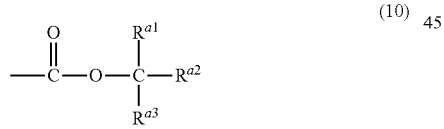

(a6)

The salt represented by the formula (a6-1) can be produced according to the known methods described in JP 2007-224008 A.

The acid generator of the present invention contains the salt (aa). The acid generator of the present invention can contain two or more kinds of the salt (aa). The acid generator of the present invention can contain one or more known acid generator in addition to the salt (aa). Examples of the known acid generator include those described in JP 2006-257078 A, JP 2007-224008 A and JP 2004-4561 A. When the acid generator contains one or more known acid generator in addition to the salt (aa), the ratio of the salt (aa) to the known acid generator (the salt (aa)/the known acid generator) is usually 99/1 to 1/99.

The photoresist composition of the present invention comprises the acid generator containing the salt (aa) and a resin comprising a structural unit having an acid-labile group and being insoluble or poorly soluble in an aqueous alkali solution but becoming soluble in an aqueous alkali solution by the action of an acid.

In this specification, "an acid-labile group" means a group capable of being eliminated by the action of an acid.

Examples of the acid-labile group include a group represented by the formula (10):

$$\begin{array}{c} O \quad R^{a1} \\ \| \quad | \\ -C-O-C-R^{a2} \\ | \\ R^{a3} \end{array} \quad (10)$$

wherein $R^{a1}$, $R^{a2}$ and $R^{a3}$ independently each represent a C1-C8 aliphatic hydrocarbon group or a C3-C20 alicyclic hydrocarbon group, or $R^{a1}$ and $R^{a2}$ are bonded each other to form a C3-C20 ring.

Examples of the C1-C8 aliphatic hydrocarbon group include a C1-C8 alkyl group such as a methyl group, an ethyl group, a propyl group, an isopropyl group, a butyl group, a pentyl group, a hexyl group, a heptyl group and an octyl group. The C3-C20 alicyclic hydrocarbon group may be monocyclic or polycyclic, and examples thereof include a monocyclic alicyclic hydrocarbon group such as a C3-C20 cycloalkyl group (e.g. a cyclopentyl group, a cyclohexyl group, a methylcyclohexyl group, a dimethylcyclohexyl group, a cycloheptyl group and a cyclooctyl group) and a polycyclic alicyclic hydrocarbon group such as a decahydronaphthyl group, an adamantyl group, a norbornyl group, a methylnorbornyl group, and the followings:

The alicyclic hydrocarbon group preferably has 3 to 16 carbon atoms.

Examples of the ring formed by bonding $R^{a1}$ and $R^{a2}$ each other include the following groups and the ring preferably has 3 to 12 carbon atoms.

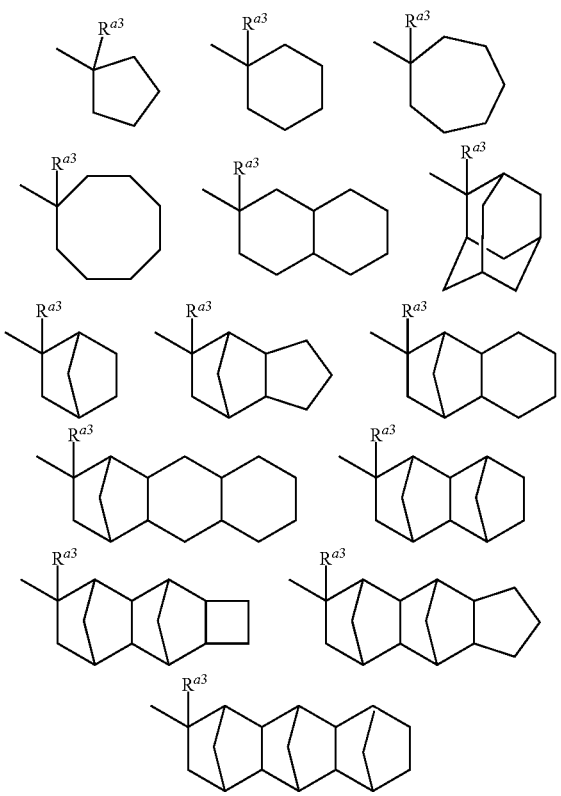

wherein $R^{a3}$ is the same as defined above.

The group represented by the formula (10) wherein $R^{a1}$, $R^{a2}$ and $R^{a3}$ independently each represent a C1-C8 alkyl group such as a tert-butyl group, the group represented by the formula (10) wherein $R^{a1}$ and $R^{a2}$ are bonded each other to form an adamantyl ring and $R^{a3}$ is a C1-C8 alkyl group such as a 2-alkyl-2-adamantyl group, and the group represented by the formula (10) wherein $R^{a1}$ and $R^{a2}$ are C1-C8 alkyl groups and $R^{a3}$ is an adamantyl group such as a 1-(1-adamantyl)-1-alkylalkoxycarbonyl group are preferable.

An acrylate monomer having an acid-labile group in its side chain or a methacryalte monomer having an acid-labile group in its side chain is preferable.

Preferable examples of the monomer include a 2-alkyl-2-adamantyl acrylate, a 2-alkyl-2-adamantyl methacrylate, 1-(1-adamantyl)-1-alkylalkyl acrylate, a 1-(1-adamantyl)-1-alkylalkyl methacrylate, a 2-alkyl-2-adamantyl 5-norbornene-2-carboxylate, a 1-(1-adamantyl)-1-alkylalkyl 5-norbornene-2-carboxylate, a 2-alkyl-2-adamantyl α-chloroacrylate and a 1-(1-adamantyl)-1-alkylalkyl α-chloroacrylate. Particularly when the 2-alkyl-2-adamantyl acrylate or the 2-alkyl-2-adamantyl methacrylate is used, a photoresist composition having excellent resolution tends to be obtained. Typical examples thereof include 2-methyl-2-adamantyl acrylate, 2-methyl-2-adamantyl methacrylate, 2-ethyl-2-adamantyl acrylate, 2-ethyl-2-adamantyl methacrylate, 2-isopropyl-2-adamantyl acrylate, 2-isopropyl-2-adamantyl methacrylate, 2-butyl-2-adamantyl acrylate, 2-methyl-2-adamantyl α-chloroacrylate and 2-ethyl-2-adamantyl α-chloroacrylate. When particularly 2-ethyl-2-adamantyl acrylate, 2-ethyl-2-adamantyl methacrylate, 2-isopropyl-2-adamantyl acrylate or 2-isopropyl-2-adamantyl methacrylate is used, a photoresist composition having excellent sensitivity and heat resistance tends to be obtained.

The 2-alkyl-2-adamantyl acrylate can be usually produced by reacting a 2-alkyl-2-adamantanol or a metal salt thereof with an acrylic halide, and the 2-alkyl-2-adamantyl methacrylate can be usually produced by reacting a 2-alkyl-2-adamantanol or a metal salt thereof with a methacrylic halide.

Two or more kinds of monomers having a group or groups dissociated by the action of the acid may be used together, if necessary.

The content of the structural unit having an acid-labile group in its resin is usually 10 to 80% by mole based on total molar of all the structural units of the resin.

The resin preferably contains one or more structural units having one or more highly polar substituents. Examples of the structural unit having one or more highly polar substituents include a structural unit having a hydrocarbon group having at least one selected from the group consisting of a hydroxyl group, a cyano group, a nitro group and an amino group and a structural unit having a hydrocarbon group having one or more —CO—O—, —CO—, —O—, —SO$_2$— or —S—. A structural unit having a saturated cyclic hydrocarbon group having a cyano group or a hydroxyl group, a structural unit having a saturated cyclic hydrocarbon group in which one or more —CH$_2$— replaced by —O— or —CO—, and a structural unit having a lactone structure in its side chain are preferable, and a structural unit having a bridged hydrocarbon group having one or more hydroxyl groups, and a structural unit having a bridged hydrocarbon group having —CO—O— or —CO— are more preferable. Examples thereof include a structural unit derived from 2-norbornene having one or more hydroxyl groups, a structural unit derived from acrylonitrile or methacrylonitrile, a structural unit derived from hydroxyl-containing adamantyl acrylate or hydroxyl-containing adamantyl methacrylate, a structural unit derived from styrene monomer such as p-hydroxystyrene and m-hydroxystyrene, a structural unit derived from a structural unit derived from 1-adamantyl acrylate or 1-adamantyl methacrylate, and a structural unit derived from acryloyloxy-γ-butyrolactone or methacryloyloxy-γ-butyrolactone having a lactone ring which may have an alkyl group.

Specific examples of the structural unit derived from hydroxyl-containing adamantyl acrylate or hydroxyl-containing adamantyl methacrylate include a structural unit derived from 3-hydroxy-1-adamantyl acrylate; a structural unit derived from 3-hydroxy-1-adamantyl methacrylate; a structural unit derived from 3,5-dihydroxy-1-adamantyl acrylate; and a structural unit derived from 3,5-dihydroxy-1-adamantyl methacrylate.

3-Hydroxy-1-adamantyl acrylate, 3-hydroxy-1-adamantyl methacrylate, 3,5-dihydroxy-1-adamantyl acrylate and 3,5-dihydroxy-1-adamantyl methacrylate can be produced, for example, by reacting corresponding hydroxyadamantane with acrylic acid, methacrylic acid or its acid halide, and they are also commercially available.

When the resin has a structural unit derived from hydroxyl-containing adamantyl acrylate or hydroxyl-containing adamantyl methacrylate, the content thereof is preferably 5 to 50% by mole based on 100% by mole of all the structural units of the resin.

Examples of the structural unit derived from a monomer having a lactone ring which may have an alkyl group include a structural unit derived from acryloyloxy-γ-butyrolactone, a structural unit derived from methacryloyloxy-γ-butyrolactone and structural units represented by the formulae (a) and (b):

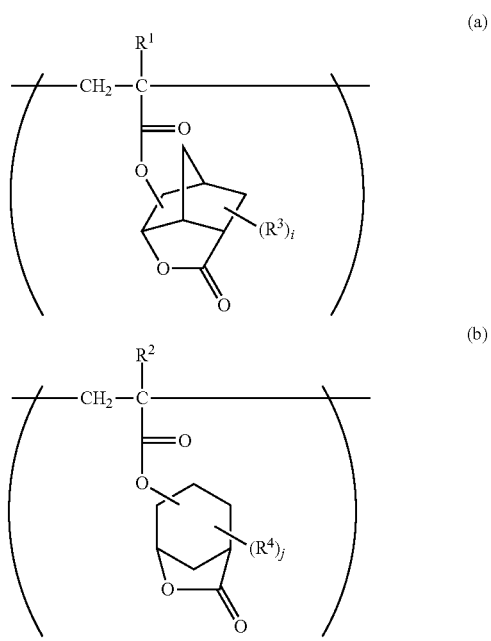

wherein $R^1$ and $R^2$ independently each represents a hydrogen atom or a methyl group, $R^3$ and $R^4$ are independently in each occurrence a hydrogen atom, a methyl group, a trifluoromethyl group or a halogen atom, and i and j independently each represents an integer of 1 to 3.

Further, the acryloyloxy-γ-butyrolactone and the methacryloyloxy-γ-butyrolactone can be produced by reacting corresponding α- or β-bromo-γ-butyrolactone with acrylic acid or methacrylic acid, or reacting corresponding α- or β-hydroxy-γ-butyrolactone with the acrylic halide or the methacrylic halide.

Examples of the monomers giving structural units represented by the formulae (a) and (b) include an acrylate of alicyclic lactones and a methacrylate of alicyclic lactones having the hydroxyl group described below, and mixtures thereof. These esters can be produced, for example, by reacting the corresponding alicyclic lactone having the hydroxyl group with acrylic acid or methacrylic acid, and the production method thereof is described in, for example, JP 2000-26446 A.

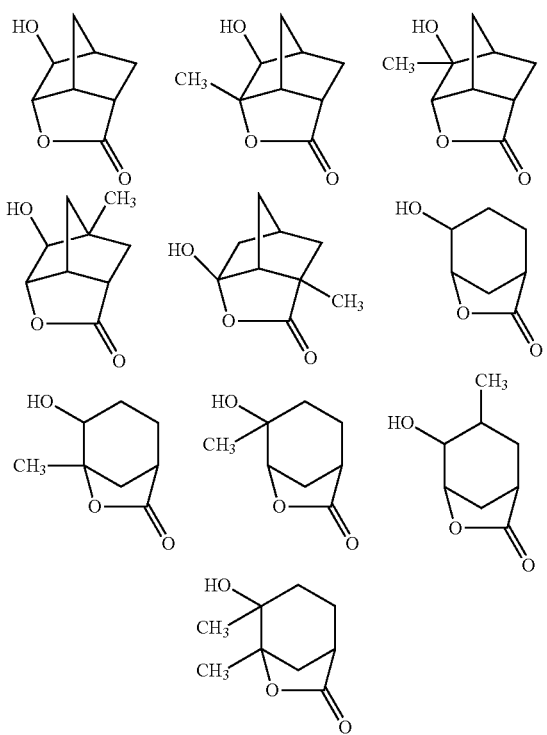

Examples of the acryloyloxy-γ-butyrolactone and the methacryloyloxy-γ-butyrolactone in which lactone ring may be substituted with the alkyl group include α-acryloyloxy-γ-butyrolactone, α-methacryloyloxy-γ-butyrolactone, α-acryloyloxy-β,β-dimethyl-γ-butyrolactone, α-methacryloyloxy-β,β-dimethyl-γ-butyrolactone, α-acryloyloxy-α-methyl-γ-butyrolactone, α-methacryloyloxy-α-methyl-γ-butyrolactone, β-acryloyloxy-γ-butyrolactone, β-methacryloyloxy-γ-butyrolactone and β-methacryloyloxy-α-methyl-γ-butyrolactone.

When the resin has a structural unit derived from a monomer having a lactone ring which may have an alkyl group, the content thereof is preferably 5 to 50% by mole based on 100% by mole of all the structural units of the resin.

Among them, the structural unit derived from 3-hydroxy-1-adamantyl acrylate, the structural unit derived from 3-hydroxy-1-adamantyl methacrylate, the structural unit derived from 3,5-dihydroxy-1-adamantyl acrylate, the structural unit derived from 3,5-dihydroxy-1-adamantylmethacrylate, the structural unit derived from α-acryloyloxy-γ-butyrolactone, the structural unit derived from α-methacryloyloxy-γ-butyrolactone, the structural unit derived from β-acryloyloxy-γ-butyrolactone, the structural unit derived from β-methacryloyloxy-γ-butyrolactone, the structural unit represented by the formula (a) and the structural unit represented by the formula (b) are preferable, because a photoresist composition having good resolution and adhesiveness of photoresist to a substrate tends to be obtained.

When the exposing is conducted using KrF excimer laser, the resin preferably has a structural unit derived from a styrene monomer such as p-hydroxystyrene and m-hydroxystyrene, and the content thereof is preferably 5 to 90% by mole based on 100% by mole of all the structural units of the resin.

The resin can contain the other structural unit or units. Examples thereof include a structural unit derived from acrylic acid or methacrylic acid, a structural unit derived from an alicyclic compound having an olefinic double bond such as a structural unit represented by the formula (c):

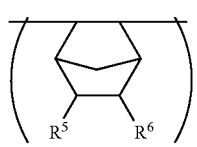

(c)

wherein $R^5$ and $R^6$ each independently represents a hydrogen atom, a C1-C3 alkyl group, a carboxyl group, a cyano group or a —COOU group in which U represents an alcohol residue, or $R^5$ and $R^6$ can be bonded together to form a carboxylic anhydride residue represented by —C(=O)OC(=O)—, a structural unit derived from an aliphatic unsaturated dicarboxylic anhydride such as a structural unit represented by the formula (d):

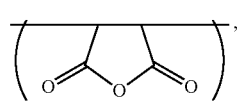

(d)

or
a structural unit represented by the formula (e):

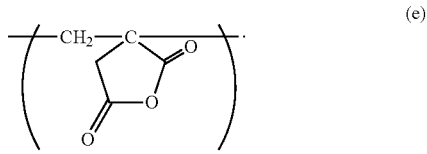

(e)

In $R^5$ and $R^6$, examples of the C1-C3 alkyl group include a methyl group, an ethyl group, a propyl group and an isopropyl group. The —COOU group is an ester formed from the carboxyl group, and examples of the alcohol residue corresponding to U include an optionally substituted C1-C8 alkyl group, 2-oxooxolan-3-yl group and 2-oxooxolan-4-yl group, and examples of the substituent on the C1-C8 alkyl group include a hydroxyl group and an alicyclic hydrocarbon group.

Specific examples of the monomer giving the structural unit represented by the above-mentioned formula (c) may include 2-norbornene, 2-hydroxy-5-norbornene, 5-norbornene-2-carboxylic acid, methyl 5-norbornene-2-carboxylate, 2-hydroxyethyl 5-norbornene-2-carboxylate, 5-norbornene-2-methanol and 5-norbornene-2,3-dicarboxylic anhydride.

When U in the —COOU group is the acid-labile group, the structural unit represented by the formula (c) is a structural unit having the acid-labile group even if it has the norbornane structure. Examples of monomers giving a structural unit having the acid-labile group include tert-butyl 5-norbornene-2-carboxylate, 1-cyclohexyl-1-methylethyl 5-norbornene-2-carboxylate, 1-methylcyclohexyl 5-norbornene-2-carboxylate, 2-methyl-2-adamantyl 5-norbornene-2-carboxylate, 2-ethyl-2-adamantyl 5-norbornene-2-carboxylate, 1-(4-methylcyclohexyl)-1-methylethyl 5-norbornene-2-carboxylate, 1-(4-hydroxylcyclohexyl)-1-methylethyl 5-norbornene-2-carboxylate, 1-methyl-1-(4-oxocyclohexyl)ethyl 5-norbornene-2-carboxylate and 1-(1-adamantyl)-1-methylethyl 5-norbornene-2-carboxylate.

The resin usually has 10,000 or more of the weight-average molecular weight, preferably 10,500 or more of the weight-average molecular weight, more preferably 11,000 or more of the weight-average molecular weight, much more preferably 11,500 or more of the weight-average molecular weight, and especially preferably 12,000 or more of the weight-average molecular weight, and the resin usually has 40,000 or less of the weight-average molecular weight, preferably 39,000 or less of the weight-average molecular weight, more preferably 38,000 or less of the weight-average molecular weight, and much more preferably 37,000 or less of the weight-average molecular weight. The weight-average molecular weight can be measured with gel permeation chromatography.

The content of the resin in the photoresist composition is usually 80 to 99.9% by weight based on sum of solid component, and the content of the acid generator is usually 0.1 to 20 parts by weight based on sum of solid component. Herein, "solid component" means the components other than a solvent among all components of the photoresist composition.

The resin can be obtained by conducting polymerization reaction of the corresponding monomer or monomers. The polymerization reaction is usually carried out in the presence of a radical initiator. This polymerization reaction can be conducted according to known methods.

In the photoresist composition of the present invention, performance deterioration caused by inactivation of acid which occurs due to post exposure delay can be diminished by adding an organic base compound, particularly a nitrogen-containing organic base compound as a quencher.

Specific examples of the nitrogen-containing organic base compound include an amine compound represented by the following formulae:

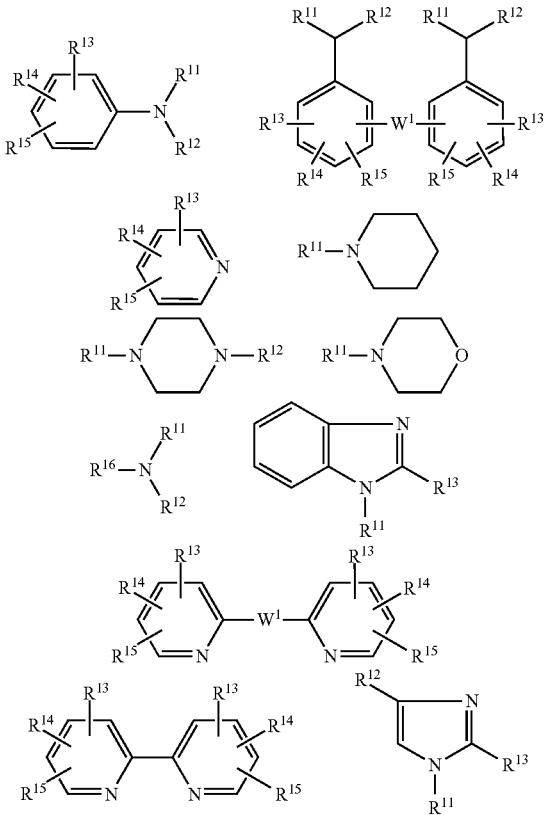

wherein $R^{11}$ and $R^{12}$ independently represent a hydrogen atom, a C1-C6 alkyl group, a C5-C10 cycloalkyl group or a C6-C10 aryl group, and the alkyl, cycloalkyl and aryl groups may be substituted with at least one group selected from the group consisting of a hydroxyl group, an amino group which may be substituted with a C1-C4 alkyl group and a C1-C6 alkoxy group which may be substituted with a C1-C6 alkoxy group, $R^{13}$ and $R^{14}$ independently represent a hydrogen atom, a C1-C6 alkyl group, a C5-C10 cycloalkyl group, a C6-C10 aryl group or a C1-C6 alkoxy group, and the alkyl, cycloalkyl, aryl and alkoxy groups may be substituted with at least one group selected from the group consisting of a hydroxyl group, an amino group which may be substituted with a C1-C4 alkyl group and a C1-C6 alkoxy group, or $R^{13}$ and $R^{14}$ bond together with the carbon atoms to which they bond to form an aromatic ring, $R^{15}$ represent a hydrogen atom, a C1-C6 alkyl group, a C5-C10 cycloalkyl group, a C6-C10 aryl group, a C1-C6 alkoxy group or a nitro group, and the alkyl, cycloalkyl, aryl and alkoxy groups may be substituted with at least one group selected from the group consisting of a hydroxyl group, an amino group which may be substituted with a C1-C4 alkyl group and a C1-C6 alkoxy group, $R^{16}$ represents a C1-C6 alkyl group or a C5-C10 cycloalkyl group, and the alkyl and cycloalkyl groups may be substituted with at least one group selected from the group consisting of a hydroxyl group, an amino group which may be substituted with a C1-C4 alkyl group and a C1-C6 alkoxy group, and $W^1$ represents —CO—, —NH—, —S—, —S—S—, a C2-C6 alkylene group, and a quaternary ammonium hydroxide represented by the following formula:

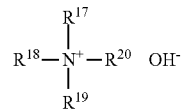

wherein $R^{17}$, $R^{18}$, $R^{19}$ and $R^{20}$ independently represent a C1-C6 alkyl group, a C5-C10 cycloalkyl group or a C6-C10 aryl group, and the alkyl, cycloalkyl and aryl groups may be substituted with at least one group selected from the group consisting of a hydroxyl group, an amino group which may be substituted with a C1-C4 alkyl group and a C1-C6 alkoxy group.

Examples of the amino group which may be substituted with the C1-C4 alkyl group include an amino group, a methylamino group, an ethylamino group, a butylamino group, a dimethylamino group and a diethylamino group. Examples of the C1-C6 alkoxy group which may be substituted with the C1-C6 alkoxy group include a methoxy group, an ethoxy group, a propoxy group, an isopropoxy group, a butoxy group, a tert-butoxy group, a pentyloxy group, a hexyloxy group and a 2-methoxyethoxy group.

Specific examples of the C1-C6 alkyl group which may be substituted with at least one group selected from the group consisting of a hydroxyl group, an amino group which may be substituted with a C1-C4 alkyl group, and a C1-C6 alkoxy group which may be substituted with a C1-C6 alkoxy group include a methyl group, an ethyl group, a propyl group, an isopropyl group, a butyl group, a tert-butyl group, a pentyl group, a hexyl group, a 2-(2-methoxyethoxy)ethyl group, a 2-hydroxyethyl group, a 2-hydroxypropyl group, a 2-aminoethyl group, a 4-aminobutyl group and a 6-aminohexyl group.

Specific examples of the C5-C10 cycloalkyl group which may be substituted with at least one group selected from the group consisting of a hydroxyl group, an amino group which may be substituted with a C1-C4 alkyl group and a C1-C6 alkoxy group include a cyclopentyl group, a cyclohexyl group, a cycloheptyl group and a cyclooctyl group.

Specific examples of the C6-C10 aryl group which may be substituted with at least one group selected from the group consisting of a hydroxyl group, an amino group which may be substituted with a C1-C4 alkyl group or a C1-C6 alkoxy group include a phenyl group and a naphthyl group.

Specific examples of the C1-C6 alkoxy group include a methoxy group, an ethoxy group, a propoxy group, an isopropoxy group, a butoxy group, a tert-butoxy group, a pentyloxy group and a hexyloxy group.

Specific examples of the C2-C6 alkylene group include an ethylene group, a trimethylene group and a tetramethylene group.

Specific examples of the amine compound include hexylamine, heptylamine, octylamine, nonylamine, decylamine, aniline, 2-methylaniline, 3-methylaniline, 4-methylaniline, 4-nitroaniline, 1-naphthylamine, 2-naphthylamine, ethylenediamine, tetramethylenediamine, hexamethylenediamine, 4,4'-diamino-1,2-diphenylethane, 4,4'-diamino-3,3'-dimethyldiphenylmethane, 4,4'-diamino-3,3'-diethyldiphenylmethane, dibutylamine, dipentylamine, dihexylamine, diheptylamine, dioctylamine, dinonylamine, didecylamine, N-methylaniline, piperidine, diphenylamine, triethylamine, trimethylamine, tripropylamine, tributylamine, tripentylamine, trihexylamine, triheptylamine, trioctylamine, trinonylamine, tridecylamine, methyldibutylamine, methyldipentylamine, methyldihexylamine, methyldicyclohexylamine, methyldiheptylamine, methyldioctylamine, methyldinonylamine, methyldidecylamine, ethyldibutylamine, ethyldipentylamine, ethyldihexylamine, ethyldiheptylamine, ethyldioctylamine, ethyldinonylamine, ethyldidecylamine, dicyclohexylmethylamine, tris[2-(2-methoxyethoxy)ethyl]amine, triisopropanolamine, N,N-dimethylaniline, 2,6-diisopropylaniline, imidazole, benzimidazole, pyridine, 4-methylpyridine, 4-methylimidazole, bipyridine, 2,2'-dipyridylamine, di-2-pyridyl ketone, 1,2-di(2-pyridyl)ethane, 1,2-di(4-pyridyl)ethane, 1,3-di(4-pyridyl)propane, 1,2-bis(2-pyridyl)ethylene, 1,2-bis(4-pyridyl)ethylene, 1,2-bis(4-pyridyloxy)ethane, 4,4'-dipyridyl sulfide, 4,4'-dipyridyl disulfide, 1,2-bis(4-pyridyl)ethylene, 2,2'-dipicolylamine and 3,3'-dipicolylamine.

Examples of the quaternary ammonium hydroxide include tetramethylammonium hydroxide, tetrabutylammonium hydroxide, tetrahexylammonium hydroxide, tetraoctylammonium hydroxide, phenyltrimethylammonium hydroxide, (3-trifluoromethylphenyl)trimethylammonium hydroxide and (2-hydroxyethyl)trimethylammonium hydroxide (so-called "choline").

A hindered amine compound having a piperidine skeleton as disclosed in JP 11-52575 A1 can be also used as the quencher.

In the point of forming patterns having higher resolution, the quaternary ammonium hydroxide is preferably used as the quencher.

When the basic compound is used as the quencher, the present resist composition preferably includes 0.01 to 1% by weight of the basic compound based on sum of solid component.

The present resist composition can contain, if necessary, a small amount of various additives such as a sensitizer, a dissolution inhibitor, other polymers, a surfactant, a stabilizer and a dye as long as the effect of the present invention is not prevented.

The present resist composition is usually in the form of a resist liquid composition in which the above-mentioned ingredients are dissolved in a solvent and the resist liquid composition is applied onto a substrate such as a silicon wafer by a conventional process such as spin coating. The solvent used is sufficient to dissolve the above-mentioned ingredients, have an adequate drying rate, and give a uniform and smooth coat after evaporation of the solvent. Solvents generally used in the art can be used.

Examples of the solvent include a glycol ether ester such as ethyl cellosolve acetate, methyl cellosolve acetate and propylene glycol monomethyl ether acetate; an acyclic ester such as ethyl lactate, butyl acetate, amyl acetate and ethyl pyruvate; a ketone such as acetone, methyl isobutyl ketone, 2-heptanone and cyclohexanone; and a cyclic ester such as γ-butyrolactone. These solvents may be used alone and two or more thereof may be mixed to use.

A photoresist pattern can be produced by the following steps (1) to (5):

(1) a step of applying the photoresist composition of the present invention on a substrate, (2) a step of forming a photoresist film by conducting drying, (3) a step of exposing the photoresist film to radiation, (4) a step of baking the exposed photoresist film, and (5) a step of developing the baked photoresist film with an alkaline developer, thereby forming a photoresist pattern.

The applying of the photoresist composition on a substrate is usually conducted using a conventional apparatus such as spin coater.

The formation of the photoresist film is usually conducted using a heating apparatus such as hot plate or a decompressor, and the heating temperature is usually 50 to 200° C., and the operation pressure is usually 1 to $1.0*10^5$ Pa.

The photoresist film obtained is exposed to radiation using an exposure system. The exposure is usually conducted through a mask having a pattern corresponding to the desired photoresist pattern. Examples of the exposure source include a light source radiating laser light in a UV-region such as a KrF excimer laser (wavelength: 248 nm), an ArF excimer laser (wavelength: 193 nm) and a $F_2$ laser (wavelength: 157 nm), and a light source radiating harmonic laser light in a far UV region or a vacuum UV region by wavelength conversion of laser light from a solid laser light source (such as YAG or semiconductor laser).

The temperature of baking of the exposed photoresist film is usually 50 to 200° C., and preferably 70 to 150° C.

The development of the baked photoresist film is usualt carried out using a development apparatus. The alkaline developer used may be any one of various alkaline aqueous solution used in the art. Generally, an aqueous solution of tetramethylammonium hydroxide or (2-hydroxyethyl)trimethylammonium hydroxide (commonly known as "choline") is often used. After development, the photoresist pattern formed is preferably washed with ultrapure water, and the remained water on the photoresist pattern and the substrate is preferably removed.

The salt of the present invention and the polymer of the present invention are suitable components of a photoresist composition, and the photoresist composition of the present invention provides a photoresist pattern showing good resolution and good focus margin, and therefore, the photoresist composition of the present invention is suitable for ArF excimer laser lithography, KrF excimer laser lithography, ArF immersion lithography, EUV (extreme ultraviolet) lithography, EUV immersion lithography and EB (electron beam) lithography. Further, the photoresist composition of the present invention can be used for an immersion lithography and for a dry lithography. Furthermore, the photoresist composition of the present invention can be also used for a double imaging lithography.

EXAMPLES

The present invention will be described more specifically by Examples, which are not construed to limit the scope of the present invention.

The "%" and "part(s)" used to represent the content of any component and the amount of any material used in the following examples and comparative examples are on a weight basis unless otherwise specifically noted. The weight-average molecular weight of any material used in the following examples is a value found by gel permeation chromatography [HLC-8120GPC Type, Column (Three Columns with guard column): TSKgel Multipore HXL-M, manufactured by TOSOH CORPORATION, Solvent: Tetrahydrofuran, Flow rate: 1.0 mL/min., Detector: RI detector, Column temperature: 40° C., Injection volume: 100 μL] using standard polystyrene as a standard reference material. Structures of compounds were determined by NMR (GX-270 Type or EX-270 Type, manufactured by JEOL LTD.) and mass spectrometry (Liquid Chromatography: 1100 Type, manufactured by AGILENT TECHNOLOGIES LTD., Mass Spectrometry: LC/MSD Type or LC/MSD TOF Type, manufactured by AGILENT TECHNOLOGIES LTD.).

Example 1

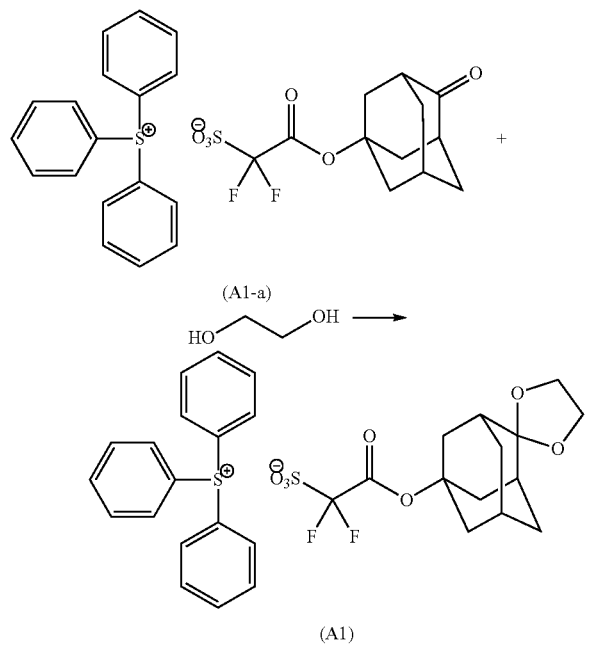

The salt represented by the formula (A1-a) was produced according to the method described in JP 2007-224008 A. A mixture of 20.00 parts of the salt represented by the formula (A1-a) and 42.32 parts of ethylene glycol was stirred at 23° C. for 30 minutes. The resultant mixture was heated up to 103° C. To the mixture, 0.17 part of sulfuric acid was added and the resultant mixture was stirred at 103° C. for 1 hour followed by cooling down to 23° C. To the obtained mixture, 200 parts of chloroform and 100 parts of ion-exchanged water were added. The resultant mixture was stirred at 23° C. for 30 minutes, and separated to an organic layer and an aqueous layer. The organic layer was washed three times with ion-exchanged water. The organic layer was concentrated and then, 40 parts of acetonitrile was added to the obtained residue. The resultant mixture was stirred at 23° C. for 30 minutes, and then, concentrated. To the obtained residue, 100 parts of ethyl acetate was added and the resultant mixture was stirred at 23° C. for 30 minutes, and then, supernatant solution was removed. The obtained residue was concentrated to obtain 17.18 parts of a salt represented by the above-mentioned formula (A1) in the form of orange oil. This is called as salt A1.

MS (ESI (+) Spectrum): $M^+$ 263.1
MS (ESI (−) Spectrum): $M^-$ 367.1
$^1$H-NMR (dimethylsulfoxide-$d_6$, Internal Standard: tetramethylsilane): δ (ppm) 1.50-1.60 (m, 2H), 1.70-1.85 (m, 2H), 1.85-2.10 (m, 7H), 2.18-2.30 (m, 2H), 3.86 (m, 4H), 7.70-7.90 (m, 15H)

Examples 2

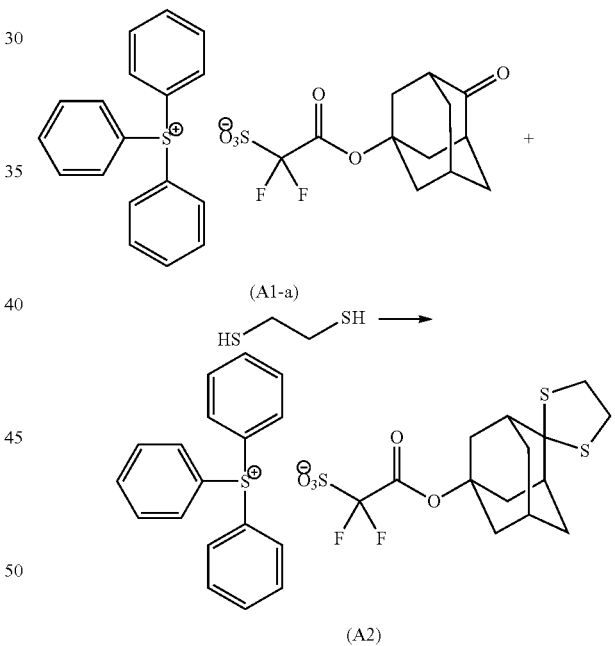

A mixture of 10.00 parts of the salt represented by the formula (A1-a), 1.60 parts of 1,2-ethanedithiol and 60.00 parts of chloroform was stirred at 23° C. for 30 minutes. To the mixture, 0.70 part of zinc chloride was added and the resultant mixture was stirred at 23° C. for 3 hours, and then, the obtained mixture was stirred at 60° C. for 1 hour followed by cooling down to 23° C. The obtained mixture was filtrated and the obtained filtrate was concentrated. To the obtained residue, 17 parts of chloroform and 8.5 parts of ion-exchanged water were added. The resultant mixture was stirred at 23° C. for 30 minutes, and separated to an organic layer and an aqueous layer. The organic layer was washed three times with ion-exchanged water. The organic layer was concentrated and then, 7.45 parts of acetonitrile was added to the obtained residue. The resultant mixture was stirred at 23° C. for 30 minutes, and then, concentrated. To the obtained residue, 6.16 parts of acetonitrile and 3.24 parts of ethyl acetate were added and the resultant mixture was stirred at 23° C. for 30 minutes, and then, filtrated to obtain 5.54 parts of a salt represented by the above-mentioned formula (A2). This is called as salt A2.

MS (ESI (+) Spectrum): $M^+$ 263.1
MS (ESI (−) Spectrum): $M^-$ 399.0
$^1$H-NMR (dimethylsulfoxide-$d_6$, Internal Standard: tetramethylsilane): δ (ppm) 1.65-1.73 (m, 2H), 1.94-2.00 (m, 2H), 2.05-2.15 (m, 5H), 2.20-2.24 (m, 2H), 2.42-2.47 (m, 2H), 3.25 (m, 4H), 7.70-7.90 (m, 15H)

Example 3

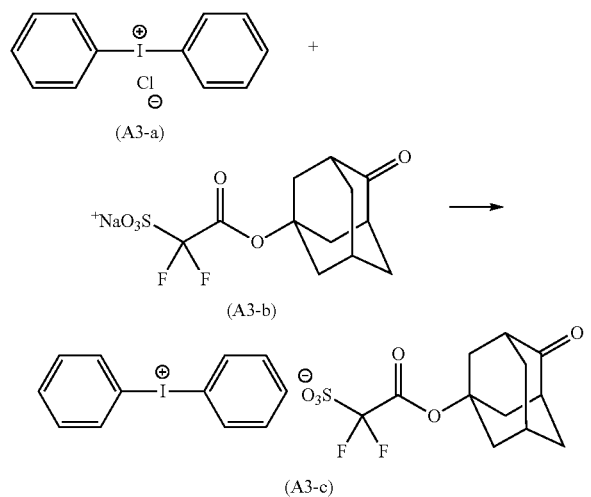

30 minutes, and filtrated to obtain 1.48 parts of the salt represented by the formula (A3-c).

A mixture of 1.30 parts of the salt represented by the formula (A3-c), 0.16 part of 1,2-ethanedithiol and 6.00 parts of chloroform was stirred at 23° C. for 30 minutes. To the mixture, 0.07 part of zinc chloride was added and the resultant mixture was stirred at 23° C. for 3 hours, and then, the obtained mixture was stirred at 60° C. for 1 hour followed by cooling down to 23° C. The obtained mixture was filtrated and the obtained filtrate was concentrated. To the obtained residue, 10 parts of chloroform and 5 parts of ion-exchanged water were added. The resultant mixture was stirred at 23° C. for 30 minutes, and separated to an organic layer and an aqueous layer. The organic layer was washed three times with ion-exchanged water. The organic layer was concentrated and then, 5 parts of acetonitrile was added to the obtained residue. The resultant mixture was stirred at 23° C. for 30 minutes, and then, concentrated. To the obtained residue, 3.0 parts of acetonitrile, 1.0 part of tert-butyl methyl ether and 1.0 part of ethyl acetate were added and the resultant mixture was stirred at 23° C. for 1 hour, and then, filtrated to obtain 0.32 part of a salt represented by the above-mentioned formula (A3). This is called as salt A3.

MS (ESI (+) Spectrum): $M^+$ 281.0
MS (ESI (−) Spectrum): $M^-$ 399.0
$^1$H-NMR (dimethylsulfoxide-$d_6$, Internal Standard: tetramethylsilane): δ (ppm) 1.65-1.73 (m, 2H), 1.94-2.00 (m, 2H), 2.05-2.15 (m, 5H), 2.20-2.24 (m, 2H), 2.42-2.47 (m, 2H), 3.25 (m, 4H), 7.40-7.49 (m, 4H), 7.52-7.60 (m, 2H), 8.10-8.19 (m, 4H)

Example 4

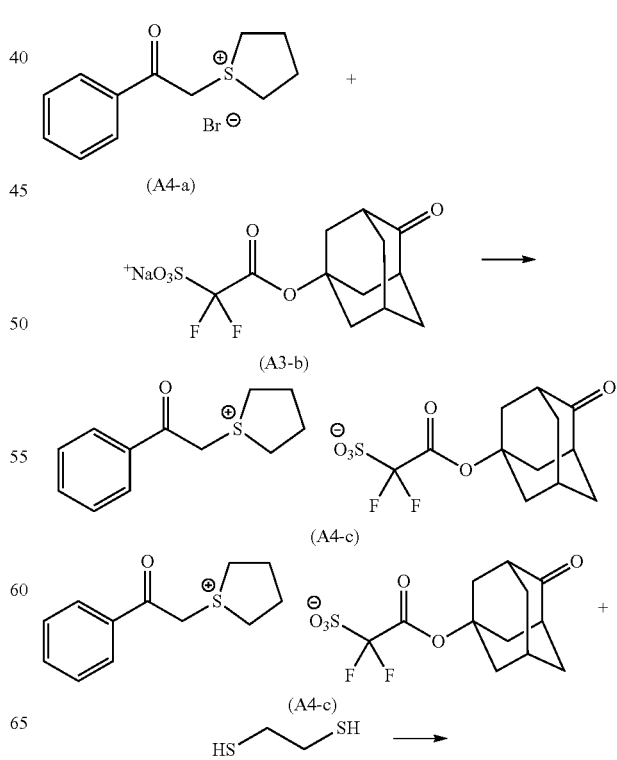

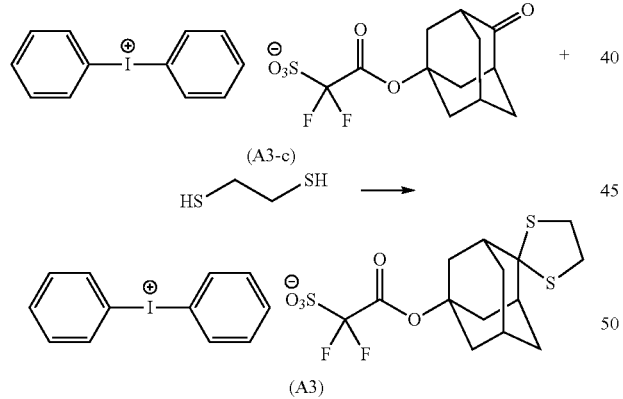

The salt represented by the formula (A3-b) was produced according to the method described in JP 2007-224008 A. To a mixture of 5.4 parts of the salt represented by the formula (A3-b), of which purity was 35.6%, 40 parts of chloroform and 20 parts of ion-exchanged water, 1.80 parts of the salt represented by the formula (A3-a) and 20 parts of ion-exchanged water were added. The resultant mixture was stirred at 23° C. for 15 hours. The mixture was separated to an organic layer and an aqueous layer. The organic layer was washed with 20 parts of ion-exchanged water. This washing was repeated three times. The organic layer was concentrated and the obtained residue was mixed with 20 parts of tert-butyl methyl ether. The obtained mixture was stirred at 23° C. for -continued

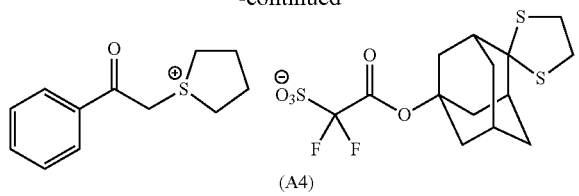

(A4)

The salt represented by the formula (A3-b) was produced according to the method described in JP 2007-224008 A. To a mixture of 5.4 parts of the salt represented by the formula (A3-b), of which purity was 35.6%, 40 parts of chloroform and 20 parts of ion-exchanged water, 1.63 parts of the salt represented by the formula (A4-a) and 20 parts of ion-exchanged water were added. The resultant mixture was stirred at 23° C. for 15 hours. The mixture was separated to an organic layer and an aqueous layer. The organic layer was washed with 20 parts of ion-exchanged water. This washing was repeated three times. The organic layer was concentrated and the obtained residue was mixed with 20 parts of tert-butyl methyl ether. The obtained mixture was stirred at 23° C. for 30 minutes, and filtrated to obtain 1.18 parts of the salt represented by the formula (A4-c).

A mixture of 1.14 parts of the salt represented by the formula (A4-c), 0.16 part of 1,2-ethanedithiol and 6.00 parts of chloroform was stirred at 23° C. for 30 minutes. To the mixture, 0.07 part of zinc chloride was added and the resultant mixture was stirred at 23° C. for 3 hours, and then, the obtained mixture was stirred at 60° C. for 1 hour followed by cooling down to 23° C. The obtained mixture was filtrated and the obtained filtrate was concentrated. To the obtained residue, 10 parts of chloroform and 5 parts of ion-exchanged water were added. The resultant mixture was stirred at 23° C. for 30 minutes, and separated to an organic layer and an aqueous layer. The organic layer was washed three times with ion-exchanged water. The organic layer was concentrated and then, 3 parts of acetonitrile was added to the obtained residue. The resultant mixture was stirred at 23° C. for 30 minutes, and then, concentrated. To the obtained residue, 5 parts of ethyl acetate was added and then, the resultant mixture was stirred and supernatant solution was removed. The obtained residue was concentrated. To the obtained residue, 1 part of acetonitrile and 5 parts of tert-butyl methyl ether were added and the resultant mixture was stirred. The supernatant solution was removed, and the obtained residue was concentrated. To the obtained residue, 5 parts of ethyl acetate was added and the resultant mixture was stirred. The supernatant solution was removed, and the obtained residue was mixed with 5 parts of tert-butyl methyl ether. The resultant mixture was stirred, and then, the supernatant solution was removed. The obtained residue was dissolved in chloroform and the resultant solution was concentrated to obtain 0.18 part of a salt represented by the above-mentioned formula (A4). This is called as salt A4.

MS (ESI (+) Spectrum): M$^+$ 207.1

MS (ESI (−) Spectrum): M$^−$ 399.0

$^1$H-NMR (dimethylsulfoxide-d$_6$, Internal Standard: tetramethylsilane): δ (ppm) 1.65-1.73 (m, 2H), 1.94-2.00 (m, 2H), 2.05-2.35 (m, 11H), 2.42-2.47 (m, 2H), 3.25 (m, 4H), 3.43-3.69 (m, 4H), 5.31 (s, 2H), 7.58-7.69 (m, 2H), 7.73-7.84 (m, 1H), 7.95-8.05 (m, 2H)

Example 5

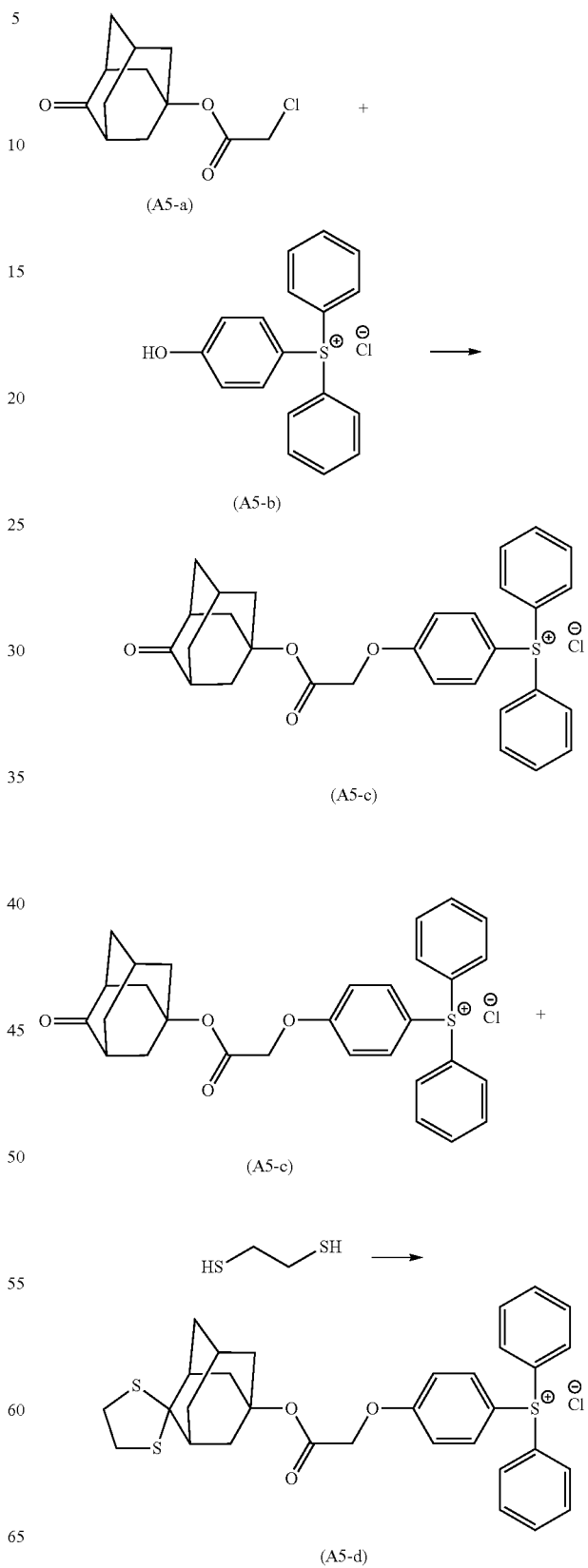

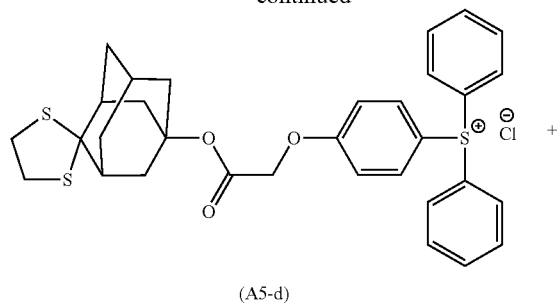

(A5-d)

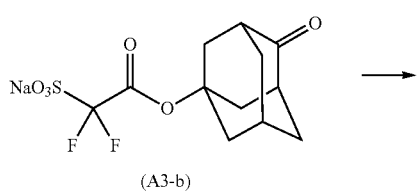

(A3-b)

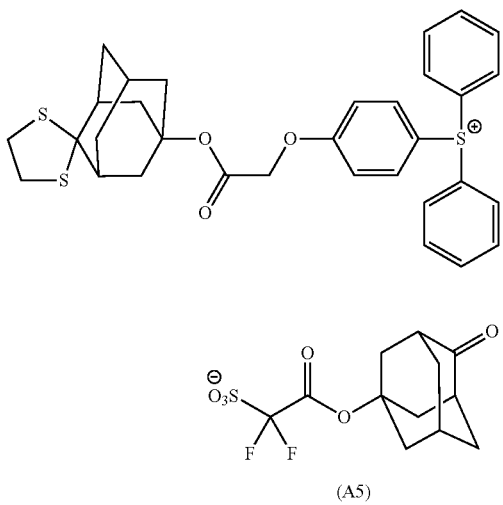

(A5)

A mixture of 4.85 parts of the compound represented by the formula (A5-a) and 28.00 parts of N,N-dimethylformamide was stirred at 23° C. for 30 minutes. To the obtained mixture, 1.66 parts of potassium carbonate and 0.84 parts of potassium iodide were added and the resultant mixture was stirred at 50° C. for 1 hour. The obtained mixture was cooled at 40° C., and a solution prepared by dissolving 6.30 parts of the salt represented by the formula (A5-b) in 28.00 parts of N,N-dimethylformamide was added dropwise thereto over 1 hour. The obtained mixture was stirred at 75° C. for 5 hours, and then, cooled down to 23° C. To the mixture, 60.00 parts of chloroform and 60.00 parts of 1N hydrochloric acid were added, and the resultant mixture was separated to an organic layer and an aqueous layer. The organic layer was repeated to wash with 60.00 parts of ion-exchanged water until the aqueous layer showed neutral. The organic layer was mixed with 2.0 parts of active carbon and the resultant mixture was stirred and then, filtrated. The obtained filtrate was concentrated and the obtained residue was mixed with 20 parts of ethyl acetate. The resultant mixture was stirred and then, the supernatant solution was removed. The obtained residue was mixed with 20 parts of tert-butyl methyl ether. The resultant mixture was stirred and then, the supernatant solution was removed. The obtained residue was dissolved in chloroform, and the obtained solution was concentrated to obtain 5.02 parts of the salt represented by the formula (A5-c).

A mixture of 5.00 parts of the salt represented by the formula (A5-c), 0.90 part of 1,2-ethanedithiol and 30.00 parts of chloroform was stirred at 23° C. for 30 minutes. To the mixture, 0.35 part of zinc chloride was added and the resultant mixture was stirred at 23° C. for 3 hours, and then, the obtained mixture was stirred at 60° C. for 1 hour followed by cooling down to 23° C. The obtained mixture was filtrated and the obtained filtrate was concentrated. To the obtained residue, 50 parts of chloroform and 25 parts of ion-exchanged water were added. The resultant mixture was stirred at 23° C. for 30 minutes, and separated to an organic layer and an aqueous layer. The organic layer was washed three times with ion-exchanged water. The organic layer was concentrated and then, 15 parts of acetonitrile was added to the obtained residue. The resultant mixture was stirred at 23° C. for 30 minutes, and then, concentrated. To the obtained residue, 15 parts of ethyl acetate was added and then, the resultant mixture was stirred and supernatant solution was removed. The obtained residue was concentrated. To the obtained residue, 15 parts of tert-butyl methyl ether was added and the resultant mixture was stirred. The supernatant solution was removed, and the obtained residue was concentrated. The obtained residue was dissolved in chloroform and the resultant solution was concentrated to obtain 2.88 parts of a salt represented by the above-mentioned formula (A5-d).

The salt represented by the formula (A3-b) was produced according to the method described in JP 2007-224008 A. To a mixture of 2.7 parts of the salt represented by the formula (A3-b), of which purity was 35.6%, 20 parts of chloroform and 10 parts of ion-exchanged water, 1.70 parts of the salt represented by the formula (A5-d) and 10 parts of ion-exchanged water were added. The resultant mixture was stirred at 23° C. for 15 hours. The mixture was separated to an organic layer and an aqueous layer. The organic layer was washed with 10 parts of ion-exchanged water. This washing was repeated three times. The organic layer was concentrated and the obtained residue was mixed with 10 parts of acetonitrile. The resultant mixture was stirred at 23° C. for 30 minutes, and then, concentrated. The obtained residue was mixed with 10 parts of ethyl acetate, and the resultant mixture was stirred at 23° C. for 30 minutes, and then, supernatant solution was removed. The obtained residue was concentrated. The obtained residue was mixed with 10 parts of tert-butyl methyl ether. The obtained mixture was stirred at 23° C. for 30 minutes, and then, the supernatant solution was removed. The obtained residue was concentrated. The obtained residue was dissolved in chloroform and the resultant solution was concentrated to obtain 1.28 parts of a salt represented by the above-mentioned formula (A5). This is called as salt A5.

MS (ESI (+) Spectrum): $M^+$ 561.2

MS (ESI (−) Spectrum): $M^-$ 323.0

$^1$H-NMR (dimethylsulfoxide-$d_6$, Internal Standard: tetramethylsilane): δ (ppm) 1.83 (m, 4H), 1.98-2.00 (m, 4H), 2.21-2.36 (m, 14H), 2.50-2.53 (m, 4H), 3.25 (m, 4H), 4.99 (s, 2H), 7.29-7.40 (m, 2H), 7.70-7.90 (m, 12H)

Example 6

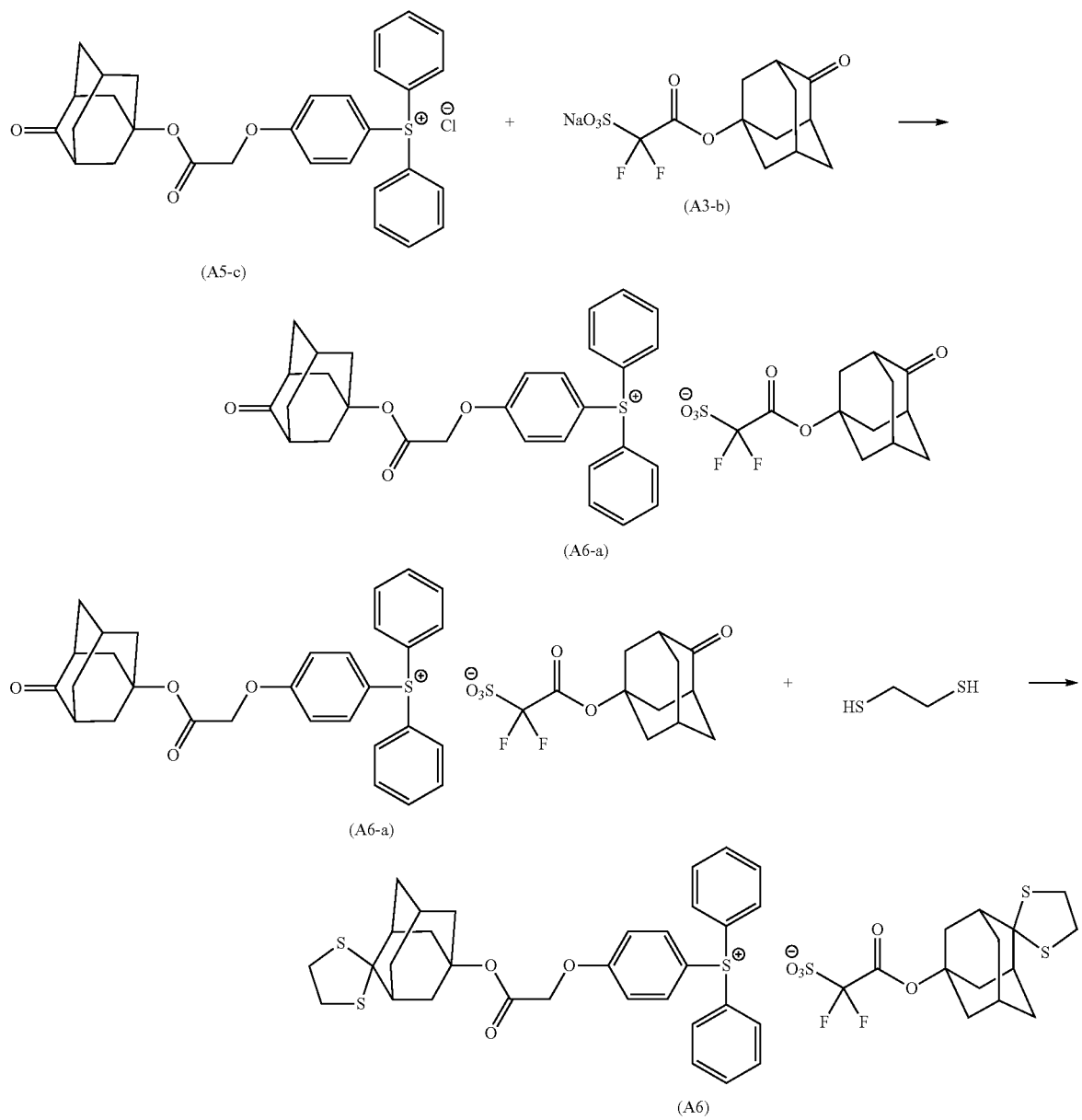

The salt represented by the formula (A3-b) was produced according to the method described in JP 2007-224008 A. To a mixture of 4.86 parts of the salt represented by the formula (A3-b), of which purity was 35.6%, 15 parts of acetonitrile and 15 parts of ion-exchanged water, 2.61 parts of the salt represented by the formula (A5-c), 5 parts of acetonitrile and 5 parts of ion-exchanged water were added. The resultant mixture was stirred for 15 hours. The mixture was concentrated. The obtained residue was extracted with 50 parts of chloroform, and the obtained organic layer was washed with 25 parts of ion-exchanged water. This washing was repeated three times. The organic layer was mixed with 1.2 parts of active carbon. The resultant mixture was stirred and then, filtrated. The obtained filtrate was concentrated and the obtained residue was mixed with 10 parts of ethyl acetate. The resultant mixture was stirred. The supernatant solution was removed, and the obtained residue was mixed with 10 parts of tert-butyl methyl ether. The obtained mixture was stirred, and the supernatant solution was removed. The obtained residue was dissolved in chloroform, and the obtained solution was concentrated to obtain 2.69 parts of the salt represented by the formula (A6-a).

A mixture of 7.76 parts of the salt represented by the formula (A6-a), 1.80 part of 1,2-ethanedithiol and 50.00 parts of chloroform was stirred at 23° C. for 30 minutes. To the mixture, 0.70 part of zinc chloride was added and the resultant mixture was stirred at 23° C. for 3 hours, and then, the obtained mixture was stirred at 60° C. for 1 hour followed by cooling down to 23° C. The obtained mixture was filtrated and the obtained filtrate was concentrated. To the obtained residue, 50 parts of chloroform and 50 parts of ion-exchanged water were added. The resultant mixture was stirred at 23° C.

for 30 minutes, and separated to an organic layer and an aqueous layer. The organic layer was washed three times with ion-exchanged water. The organic layer was concentrated and then, 30 parts of acetonitrile was added to the obtained residue. The resultant mixture was stirred at 23° C. for 30 minutes, and then, concentrated. To the obtained residue, 25 parts of ethyl acetate was added and then, the resultant mixture was stirred and supernatant solution was removed. The obtained residue was concentrated. To the obtained residue, 25 parts of tert-butyl methyl ether was added and the resultant mixture was stirred. The supernatant solution was removed, and the obtained residue was concentrated. The obtained residue was dissolved in chloroform and the resultant solution was concentrated to obtain 1.98 parts of a salt represented by the above-mentioned formula (A6). This is called as salt A6.

MS (ESI (+) Spectrum): M⁺ 561.2
MS (ESI (−) Spectrum): M⁻ 399.0
$^1$H-NMR (dimethylsulfoxide-$d_6$, Internal Standard: tetramethylsilane): δ (ppm) 1.65-1.73 (m, 2H), 1.83 (m, 2H), 1.94-2.00 (m, 4H), 2.05-2.15 (m, 5H), 2.20-2.36 (m, 9H), 2.42-2.47 (m, 2H), 2.50-2.53 (m, 2H), 3.25 (m, 8H), 4.99 (s, 2H), 7.29-7.40 (m, 2H), 7.70-7.90 (m, 12H)

Monomers used in the following Example are following monomers A, B and C.

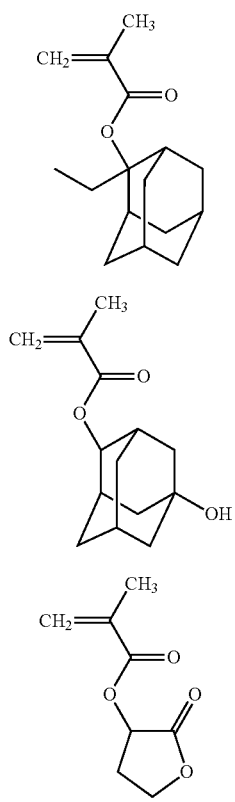

Resin Synthesis Example 1

The monomers A, B and C were mixed in a molar ratio of 50/25/25 (monomer A/monomer B/monomer C), and 1,4-dioxane in 1.5 times part based on total parts of all monomers was added to prepare a mixture. To the mixture, azobisisobutyronitrile as an initiator in a ratio of 1 mol % based on all monomer molar amount and azobis(2,4-dimethylvaleronitrile) as an initiator in a ratio of 3 mol % based on all monomer molar amount were added, and the obtained mixture was heated at 77° C. for about 5 hours. The reaction mixture obtained was poured into a mixture of a large amount of methanol and water to cause precipitation, and this operation was repeated three times for purification. As a result, a polymer having a weight-average molecular weight of about 8,000 was obtained in a yield of 60%. The polymer had the following structural units. This is called as polymer B1.

Examples 7 to 15 and Comparative Example 1

<Acid Generator>
A1, A2, A3, A4, A5, A6
C1:

<Resin>
Resin B1
<Quencher>
Q1: 2,6-diisopropylaniline

<Solvent>
Y1: propylene glycol monomethyl ether acetate 265 parts
propylene glycol monomethyl ether 20 parts
2-heptanone 20 parts
γ-butyrolactone 3.5 parts The following components were mixed and dissolved, further, filtrated through a fluorine resin filter having pore diameter of 0.2 μm, to prepare photoresist compositions.
Resin (kind and amount are described in Table 1)
Acid generator (kind and amount are described in Table 1)
Quencher (kind and amount are described in Table 1)
Solvent Y1

TABLE 1

| Ex. No. | Resin (kind/amount (part)) | Acid Generator (kind/amount (part)) | Quencher (kind/amount (part)) | Solvent (kind) |
|---|---|---|---|---|
| Ex. 7 | B1/10 | A1/0.7 | Q1/0.065 | Y1 |
| Ex. 8 | B1/10 | A1/1.5 | Q1/0.135 | Y1 |
| Ex. 9 | B1/10 | A1/0.35 | Q1/0.0325 | Y1 |
| Ex. 10 | B1/10 | A2/0.7 | Q1/0.065 | Y1 |
| Ex. 11 | B1/10 | A3/0.7 | Q1/0.065 | Y1 |
| Ex. 12 | B1/10 | A4/0.7 | Q1/0.065 | Y1 |
| Ex. 13 | B1/10 | A5/0.7 | Q1/0.065 | Y1 |
| Ex. 14 | B1/10 | A6/0.7 | Q1/0.065 | Y1 |
| Ex. 15 | B1/10 | A2/0.5 A4/0.2 | Q1/0.065 | Y1 |
| Comp. Ex. 1 | B1/10 | C1/0.7 | Q1/0.065 | Y1 |

Silicon wafers were each coated with "ARC-29", which is an organic anti-reflective coating composition available from Nissan Chemical Industries, Ltd., and then baked at 205° C. for 60 seconds, to form a 78 nm-thick organic anti-reflective coating. Each of the photoresist compositions prepared as above was spin-coated over the anti-reflective coating so that the thickness of the resulting film became 120 nm after drying. The silicon wafers thus coated with the respective photoresist compositions were each prebaked on a direct hotplate at 100° C. for 60 seconds. Using an ArF excimer stepper ("FPA-5000AS3" manufactured by CANON INC., NA=0.75, ⅔ Annular), each wafer thus formed with the respective resist film was subjected to line and space pattern exposure, with the exposure quantity being varied stepwise.

After the exposure, each wafer was subjected to post-exposure baking on a hotplate at 100° C. for 60 seconds and then to paddle development for 60 seconds with an aqueous solution of 2.38 wt % tetramethylammonium hydroxide.

Each of a dark field pattern developed on the organic anti-reflective coating substrate after the development was observed with a scanning electron microscope, the results of which are shown in Table 2. The term "dark field pattern", as used herein, means a pattern obtained by exposure and development through a reticle comprising chromium base surface (light-shielding portion) and linear glass layers (light-transmitting portion) formed in the chromium surface and aligned with each other. Thus, the dark field pattern is such that, after exposure and development, resist layer surrounding the line and space pattern remains on substrate.

Resolution: The photoresist pattern at the exposure dose that the line pattern and the space pattern become 1:1 after exposure through 100 nm line and space pattern mask and development was observed with a scanning electron microscope. When 85 nm line and space pattern was resolved, the resolution is good and its evaluation is marked by "○", and when 85 nm line and space pattern was not resolved or was resolved but the toppling of the patterns was observed, the resolution is bad and its evaluation is marked by "X".

Line Edge Roughness (LER): The photoresist pattern at the exposure dose that the line pattern and the space pattern become 1:1 after exposure through 100 nm line and space pattern mask and development was observed with a scanning electron microscope. The difference between the height of the highest point and height of the lowest point of the scabrous wall surface of the photoresist pattern was measured. When the difference is 9 nm or less, LER is good and its evaluation is marked by "○", and when the difference is more than 9 nm, LER is bad and its evaluation is marked by "X". The smaller the difference is, the better the pattern is.

Focus margin (DOF): The photoresist patterns were obtained using a 90 nm line and space pattern mask at the exposure amount where the line width of the line pattern and the space pattern became 90 nm, with the focal point distance being varied stepwise. Each of patterns developed on the organic anti-reflective coating substrate after the development were observed and the focal point distances when the patterns of which line width was 90 nm±5% (about 85.5 to 94.5 nm) were obtained were measured and the difference between the max value of the focal point distance and the minimum value of the focal point distance was calculated. When the difference is 0.60 μm or more, DOF is good and its evaluation is marked by "○", and when the difference is less than 0.60 μm, DOF is bad and its evaluation is marked by "X".

TABLE 2

| Ex. No. | Resolution | LER | DOF |
|---|---|---|---|
| Ex. 7 | ○ | ○ | ○ |
| Ex. 8 | ○ | ○ | ○ |
| Ex. 9 | ○ | ○ | ○ |
| Ex. 10 | ○ | ○ | ○ |
| Ex. 11 | ○ | ○ | ○ |
| Ex. 12 | ○ | ○ | ○ |
| Ex. 13 | ○ | ○ | ○ |
| Ex. 14 | ○ | ○ | ○ |
| Ex. 15 | ○ | ○ | ○ |
| Comp. Ex. 1 | X | X | X |

The salt of the present invention is novel and is useful as a component of a photoresist composition, and the photoresist composition containing the salt of the present invention provides a photoresist pattern having good resolution, good LER and good focus margin, and is especially suitable for ArF excimer laser lithography, KrF excimer laser lithography, ArF immersion lithography, EUV (extreme ultraviolet) lithography, EUV immersion lithography and EB (electron beam) lithography.

What is claimed is:
1. A salt having a divalent group represented by the formula (aa):

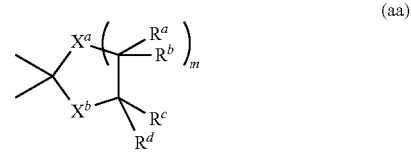

(aa)

wherein $X^a$ and $X^b$ independently each represent —O— or —S—,
$R^a$, $R^b$, $R^c$ and $R^d$ independently each represent a hydrogen atom, a C1-C4 alkyl group or a C1-C4 alkoxy group, and
m represents 1 or 2.

2. The salt according to claim 1, wherein the salt has a divalent group represented by the formula (a1):

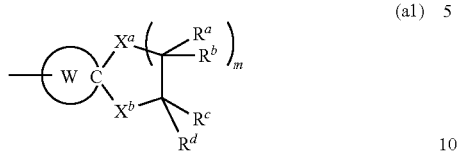
(a1)

wherein $X^a$, $X^b$, $R^a$, $R^b$, $R^c$, $R^d$ and m are the same as defined in claim 1, and W represents a C3-C36 saturated ring in which one or more —$CH_2$— can be replaced by —O—, —S—, —CO— or —$SO_2$—, and in which one or more hydrogen atoms can be replaced by a hydroxyl group, a C1-C12 alkyl group, a C1-C12 alkoxy group, a C3-C12 alicyclic hydrocarbon group or a C6-C10 aromatic hydrocarbon group.

3. The salt according to claim 1, wherein the salt consists of an anion having the divalent group represented by the formula (aa) and a cation.

4. The salt according to claim 3, wherein the cation is an organic cation.

5. The salt according to claim 3, wherein the anion is represented by the formula (a2):

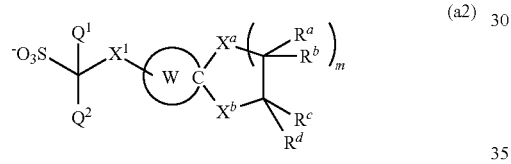
(a2)

wherein $X^a$, $X^b$, $R^a$, $R^b$, $R^c$, $R^d$ and m are the same as defined in claim 1, W is the same as defined in claim 2, $X^1$ represents a single bond or a C1-C17 saturated hydrocarbon group in which one or more —$CH_2$— can be replaced by —O— or —CO—, and $Q^1$ and $Q^2$ independently each represent a fluorine atom or a C1-C6 perfluoroalkyl group.

6. The salt according to claim 2 or 5, wherein W is a ring represented by the formula (a1-1), (a1-2) or (a1-3):

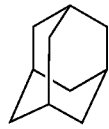
(a1-1)

(a1-2)

(a1-3)

in which one or more —$CH_2$— can be replaced by —O—, —S—, —CO— or —$SO_2$—, and in which one or more hydrogen atoms can be replaced by a hydroxyl group, a C1-C12 alkyl group, a C1-C12 alkoxy group, a C3-C12 alicyclic hydrocarbon group or a C6-C10 aromatic hydrocarbon group.

7. An acid generator comprising the salt according to claim 1.

8. A photoresist composition comprising the acid generator according to claim 7 and a resin comprising a structural unit having an acid-labile group and being insoluble or poorly soluble in an aqueous alkali solution but becoming soluble in an aqueous alkali solution by the action of an acid.

9. The photoresist composition according to claim 8, wherein the photoresist composition further contains a basic compound.

10. A process for producing a photoresist pattern comprising the following steps (1) to (5):
(1) a step of applying the photoresist composition according to claim 8 or 9 on a substrate,
(2) a step of forming a photoresist film by conducting drying,
(3) a step of exposing the photoresist film to radiation,
(4) a step of baking the exposed photoresist film, and
(5) a step of developing the baked photoresist film with an alkaline developer, thereby forming a photoresist pattern.

* * * * *